United States Patent [19]

Roszkowski et al.

[11] 4,129,661

[45] * Dec. 12, 1978

[54] 4,5-DIHYDRO-2-LOWER ALKOXYCARBONYLAMINO-4-PHENYLIMIDAZOLES AND SUBSTITUTED PHENYL DERIVATIVES THEREOF

[75] Inventors: Adolph P. Roszkowski, Saratoga; Colin C. Beard; Charles Dvorak, both of Palo Alto; Klaus Weinhardt, Redwood City, all of Calif.

[73] Assignee: Syntex (U.S.A.) Inc., Palo Alto, Calif.

[*] Notice: The portion of the term of this patent subsequent to May 9, 1995, has been disclaimed.

[21] Appl. No.: 842,655

[22] Filed: Oct. 17, 1977

Related U.S. Application Data

[63] Continuation-in-part of Ser. No. 682,682, May 3, 1976, abandoned, which is a continuation-in-part of Ser. No. 599,551, Jul. 28, 1975, abandoned.

[51] Int. Cl.² .................. A61K 31/415; C07D 233/48
[52] U.S. Cl. ................................ 424/273 R; 548/315; 548/316
[58] Field of Search ............................... 548/315, 316; 424/273 R

[56] References Cited

PUBLICATIONS

Atkins et al., J. Chem. Soc. (London) Perkin Trans. I 1973(22) pp. 2644–2646.
Matier et al., J. Med. Chem. 1973, vol. 16, pp. 901–908.
Mengelberg, Chem. Abst., 1959, vol. 53, col. 2210.

*Primary Examiner*—Natalie Trousof
*Attorney, Agent, or Firm*—Tom M. Moran

[57] ABSTRACT

4,5-Dihydro-2-lower alkoxycarbonylamino-4-phenylimidazole, and substituted phenyl derivatives thereof, and pharmaceutically acceptable salts thereof, and methods of preparing such compounds. In one method, the compounds can be prepared by treating the corresponding β-amino-β-(phenyl or substituted phenyl)-ethylamine with the desired 1,3-bis(alkoxycarbonyl)-S-methylisothiourea or 1-alkoxycarbonyl-S-methylisothiourea. The compounds can also be prepared by treating the corresponding 2-amino-4,5-dihydro-4-(phenyl or substituted phenyl)-imidazole with the desired dialkylcarbonate. The subject compounds are useful as psychotherapeutic agents for treating, preventing or palliating abnormal conditions, in mammals, which are related to the central nervous system.

77 Claims, No Drawings

4,5-DIHYDRO-2-LOWER ALKOXYCARBONYLAMINO-4-PHENYLIMIDAZOLES AND SUBSTITUTED PHENYL DERIVATIVES THEREOF

This is a continuation in part of U.S. patent application Ser. No. 682,682, filed May 3, 1976, now abandoned which is in turn a continuation-in-part of U.S. patent application Ser. No. 599,551, filed July 28, 1975, now abandoned.

BACKGROUND OF THE INVENTION

1. The Invention

This invention relates to 4,5-dihydro-2-alkoxycarbonylamino-4-(phenyl and mono- and di-substituted phenyl)-imidazoles, pharmaceutically acceptable salts thereof and methods of preparing such compounds. In another aspect, this invention relates to 4,5-dihydro-2-alkoxycarbonylamino-4-(methylenedioxyphenyl)-imidazoles, pharmaceutically acceptable salts thereof and methods of preparing such compounds.

This invention also relates to methods and compositions of treating or palliating abnormal conditions related to the central nervous system, in mammals, e.g. depression, anxiety, convulsions, centrally-induced skeletal muscle spasm and spasticity by the administration of the compounds of the invention.

2. The Prior Art

A general discussion of psychotic disorders and the use of psychotropic drugs can be found in *The Pharmacological Basis of Therapeutics*, 4th Edition, L. S. Goodman and A. Gilman eds., McMilland Co., New York (1970).

In 1973 a group of 2-amino-4-aryl-2-imidazolines were described in the *Journal of Medicinal Chemistry*, Vol. 16, No. 8, page 901 (1973), primarily as anti-hypertensive agents but were also tested for a number of other biological activities including whether the compounds reversed or prevented the effect of reserpine on mice. This publication indicated that some 2-amino-4-aryl-2-imidazolines prevented the effect of reserpine-induced ptosis, induced by the administration of 2 mg/kg of reserpine, whereas others were inactive in this test.

It is known that certain 4- or 5-aryloxazoles which are substituted at the 2-position with an acylamino, hydrocarbon aminocarbonylamino or alkoxycarbonylamino have antiinflammatory, CNS or anti-bacterial activity respectively. See, for example, Lilly's Great Britain Pat. Nos. 1,264,258 and 1,327,042 and Ajinomoto's Japanese Pat. No. 7134422. It is also known that certain 5-aryl-4-oxo-2-imidazolidinylidene ureas are useful as antisecretory agents and CNS depressants. See Belgian Pat. No. 821,099 to McNeil Labs. These compounds are entirely different from the compounds of this invention.

In contrast to the compounds described in the prior art, the compounds of the present invention are 2-alkoxycarbonylamino-4-phenyl-2-imidazolines, a number of which have been found to exhibit the ability to reverse hypothermia and ptosis induced by 5 mg/kg reserpine in laboratory animals; two well accepted assay methods for identifying compounds of clinical utility in the treatment of endogenous depression. In addition, a number of compounds of the present invention display mild tranquilizing and/or sedating properties in behavorial assays, and/or they have the ability to protect animals against various kinds of experimentally induced, convulsive seizure states and further exhibit centrally acting skeletal muscle relaxant properties. This spectrum of activities indicates that the compounds of this present invention possess a unique activity profile unlike that of any currently known psychotropic agents.

SUMMARY

In summary the compound of the invention can be represented by the following generic formula:

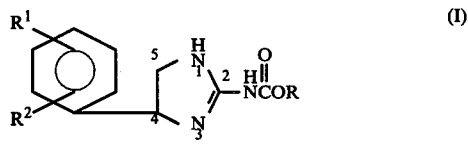

wherein R is lower alkyl; $R^1$ is hydrogen, hydroxy, lower alkyl, lower alkoxy, fluoro, chloro, bromo, iodo or trifluoromethyl and $R^2$ is hydrogen or a substituent identical to $R^1$, and wherein $R^1$ and $R^2$ can be at any different position on the phenyl ring or $R^1$ and $R^2$ together form methylenedioxy and are at adjacent carbon atoms on the phenyl ring.

Preferred compounds of this invention include those represented by formula (I), wherein (a) R is methyl, $R^1$ is hydrogen and $R^2$ is hydrogen, halo, methyl, ethyl, hydroxy, methoxy (especially at the 2- or 3- positions) alkoxy of 2-6 carbons, alkyl of 1-6 carbons or trifluoromethyl;

(b) R is methyl and $R^1$ and $R^2$ together are dihalo (especially at the 2,3-, 2,5- or 2,6- positions) dimethoxy (especially at the 2,3- or 2,5- positions), dialkoxy of 2 through 6 carbon atoms, dihydroxy, dimethyl (especially at the 2,3-, 2,4-, 2,5-, 3,5- or 2,6- positions) or diethyl;

(c) R is methyl and $R^1$ and $R^2$ together are 3,4-methylenedioxy;

(d) R is ethyl, $R^1$ is hydrogen, and $R^2$ is methoxy, ethoxy, hydroxy, hydrogen, halo, methyl or ethyl;

(e) R is ethyl and $R^1$ and $R^2$ together are dimethyl, dimethoxy, dichloro, difluoro or dihydroxy; and (f) R is lower alkyl or 3–4 carbon atoms, $R^1$ is hydrogen and $R^2$ is hydrogen, fluoro or chloro.

Pharmaceutically acceptable salts of the above compounds are also encompassed within the scope of the invention.

The preferred process of the invention comprises reacting a β-amino-β-(substituted or unsubstituted phenyl)-ethylamine, or salt thereof, having the desired phenyl substituent with 1-alkoxycarbonyl or 1,3-bis(-lower alkoxycarbonyl)-S-methylisothiourea having the desired alkoxy substituent to yield the corresponding compound of formula I.

An alternate process of the invention comprises reacting a 2-amino-4,5-dihydro-4-(substituted or unsubstituted phenyl)-imidazole, or salt therof, having the desired phenyl substituent, with a lower dialkylcarbonate, or alkyl chloroformate, having the desired alkyl substituent corresponding to R in the compounds of formula I, to yield the corresponding compound of formula I.

Another aspect of the invention comprises a method of palliating or treating abnormal conditions, in mammals, related to the central nervous system, such as depressive illness, epileptic or convulsant seizure states and other neurological disorders, anxiety and certain disorders involving muscle spasms and spasticity by the administration of an effective amount of the compounds of the invention.

Still another aspect of this invention is a pharmaceutical composition which comprises a compound of this invention and a pharmaceutically acceptable carrier.

The invention is further described hereinbelow.

FURTHER DESCRIPTION OF THE INVENTION AND PREFERRED EMBODIMENTS

Compounds

Broadly, the compounds of this invention are represented by the formula

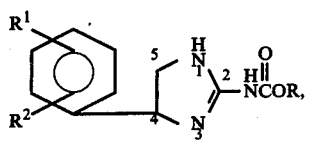

(I)

wherein R is lower alkyl; $R^1$ is hydrogen, lower alkyl, hydroxy, lower alkoxy, fluoro, chloro, bromo, iodo or trifluoromethyl and $R^2$ is hydrogen or is a substituent which is identical to the $R^1$ substituent and wherein $R^1$ and $R^2$ can each be at any different position on the phenyl ring or $R^1$ and $R^2$ together form methylenedioxy and are at adjacent carbon atoms on the phenyl ring.

Preferably, the compounds include those represented by formula (I), wherein (a) R is methyl, $R^1$ is hydrogen and $R^2$ is hydrogen, halo, methyl, ethyl, hydroxy, methoxy (especially at the 2- or 3- positions), alkoxy of 2–6 carbons, alkyl of 1–6 carbons or trifluoromethyl;

(b) R is methyl and $R^1$ and $R^2$ together are dihalo, dimethoxy (especially at the 2,3-, 2,6- 2,5- positions), dialkoxy of 2 through 6 carbon atoms, dihydroxy, dimethyl (especially at the 2,3-, 2,4-, 2,5-, 3,5- or 2,6- positions) or diethyl;

(c) R is methyl and $R^1$ and $R^2$ together are 3,4-methylenedioxy;

(d) R is ethyl, $R^1$ is hydrogen, and $R^2$ is methoxy, ethoxy, hydroxy, hydrogen, halo, methyl or ethyl;

(e) R is ethyl and $R^1$ and $R^2$ together are dihydroxy, dimethoxy, difluoro (especially at the 2,3-, 2,4-, 2,5- or 2,6- positions), dichloro or dimethyl; and (f) R is lower alkyl of 3–4 carbons, $R^1$ is hydrogen and $R^2$ is hydrogen, chloro or fluoro.

Also included as part of the invention are pharmaceutically acceptable salts of the above compounds.

The compounds of the invention have an asymmetric carbon atom (i.e. the imidazole ring carbon atom to which the phenyl group is attached) and thus exist as optically active isomer. Correspondingly, the above formulas are intended to represent the respective individual (+) and (−) optical isomers as well as mixtures thereof and accordingly the individual isomers as well as mixtures of the isomers (e.g. racemic mixtures) are encompassed within the invention. Also, although the compounds of the invention will be shown and described herein, for purposes of convenience, as 4,5-dihydro-2-alkoxycarbonylamino-4-phenylimidazoles, the compounds of the invention can exist in principle in any of the ring tautomeric forms (A:, B:, C:), or in the protonated form, as the hybrid structure D:.

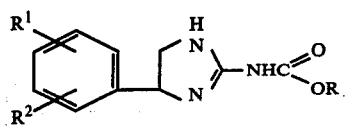

A: 4-Phenyl

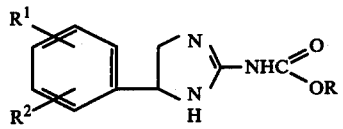

B: 5-Phenyl

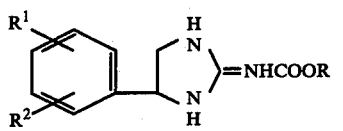

C:

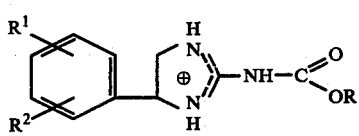

D: Anion⊖

Hence, while the compounds of the invention have been depicted as 4,5-dihydro-2-alkoxycarbonylamino-4-phenylimidazoles, for purposes of brevity and convenience, it should be understood that all of the above forms of the compounds are encompassed within the structural and word formula designations and are encompassed within the invention.

The following terms, as used hereinabove and below, have the following meanings unless expressly stated to the contrary. The term "lower alkyl" refers to alkyls having from one through six carbon atoms and includes both straight chain and branched chain alkyls such as, for example, methyl, ethyl, isopropyl, t-butyl, pentyl, n-hexyl, isohexyl, and the like. The term "lower alkyloxy" refers to alkoxy groups having from one through six carbon atoms and can be defined as the group —OR' wherein R' is lower alkyl as defined hereinabove. The term "halo" refers to the group of fluoro, chloro, bromo, and iodo.

The term "pharmaceutically acceptable salts" refers to those salts of the parent compound which do not significantly adversely affect the pharmaceutical properties (e.g. toxicity, effectiveness, etc.) of the parent compounds such as, for example, are conventionally used in the pharmaceutical art. The pharmaceutically acceptable salts of the present invention are pharmaceutically acceptable hydrogen-anion addition salts of the compounds of formula I. Suitable pharmaceutically acceptable hydrogen-anion addition salts include (expressed with respect to the anion), for example, inorganic salts such as, for example, chloride, bromide, iodide, sulfate, phosphate, nitrate, bisulfate, and the like, or organic salts such as, for example, acetate, benzoate, lactate, propionate, butyrate, valerate, tartrate, maleate, fumarate, citrate, succinate, tosylate, ascorbate, palmitate, glyconate, adipate, and the like.

The preferred pharmaceutically acceptable salts are the chloride, bromide, nitrate, maleate and citrate, and, correspondingly, the preferred salts are the corresponding salts of this group of the preferred compounds described above and hereinafter.

The term "room temperature" refers to about 20° Centigrade and all temperatures and temperature ranges refer to degrees centigrade. All percents refer to weight percents and the term "equivalent mole amount" refers to an amount stoichiometrically equivalent to the other reactant in the reaction referred to.

The compounds of the invention are useful as psychotherapeutic agents for treating, palliating, or preventing abnormal conditions, in mammals, related to the central nervous system such as depressive illness, epileptic or convulsant seizure states and other neurological disorders, anxiety and certain disorders involving muscle spasms or spasticity. Initial determination of the spectrum of psychotropic activity, in mammals, for a given compound, can, for example, be obtained by applying routine experimental procedures. For example, for antidepressant activity see Askew, *Life Sciences*, Vol. 2, page 725 (1963) and Vernier et al, *Fed. Proc.*, Vol. 21, page 419 (1962). For depressant or tranquilizing activity (i.e. treating anxiety), see Irwin, "Animal and Clinical Pharmacological Techniques" in *Drug Evaluation*, edited by J. H. Nodine et al, pages 36–54, Yearbook Medical Publishers, Inc., Chicago (1964). For anti-convulsant or anti-epileptic activity, see Swinyard, J. of Amer. Phar. Assoc., Scientific Edition, Vol. 38, page 20 (1941). For centrally acting skeletal muscle relaxant activity (based on polysynaptic transmission inhibition), King and Unna, "The Action of Mephenesin and Other Interneuron Depressants on the Brain Stem", *J. Pharmacol. Exp. Ther.*, Vol. 111, page 293 (1954) and Kamijo and Koelle; Barnett and Fiore; Europ. J. Pharmacol., Vol. 13, p. 239 (1971): *Proceedings of the Society for Experimental Biology in Medicine*, Vol. 88, pages 565–568 (1955).

Based on initial determinations, the compounds which have utility as antidepressants may be represented by formula I, wherein (a) R is methyl, $R^1$ is hydrogen and $R^2$ is hydrogen, halo, hydroxy, 2-methoxy or methyl;

(b) R is methyl and $R^1$ and $R^2$ together are dichloro, difluoro, dimethoxy or dihydroxy;

(c) R is methyl and $R^1$ and $R^2$ together are 2,6-diethoxy, 2,6-dibromo, 2,3-dibromo, 2,4-dibromo, 2,5-dibromo, 2,6-diiodo, 2,5-diiodo or 2,3-diiodo;

(d) R is ethyl and $R^1$ and $R^2$ are both hydrogen or are together 2,6-, 2,5-, 2,4-, 2,3-difluoro, 2,6-, 2,5-, 2,4- or 2,3-dihydroxy or dimethoxy;

(e) R is ethyl, $R^1$ is hydrogen and $R^2$ is halo, methyl, ethyl, methoxy, ethoxy or hydroxy; and (f) R is alkyl of 3–4 carbons, $R^1$ is hydrogen and $R^2$ is hydrogen, fluoro or chloro.

Of these, the preferred compounds are those wherein R is methyl and (a) $R^1$ is hydrogen and $R^2$ is hydrogen, hydroxy, methyl, fluoro or chloro (particularly chloro or fluoro);

(b) $R^1$ and $R^2$ together are dichloro, difluoro, dimethoxy or dihydroxy; or (c) $R^1$ and $R^2$ together are 2,6-dibromo or 2,6-diiodo.

Representative compounds include the following and their corresponding pharmaceutically acceptable salts:

4,5-dihydro-2-methoxycarbonylamino-4-phenylimidazole, 4,5-dihydro-2-ethoxycarbonylamino-4-phenylimidazole;

4,5-dihydro-2-isobutoxycarbonylamino-4-phenylimidazole;

4,5-dihydro-4-(2,6-difluorophenyl)-2-methoxycarbonylaminoimidazole;

4,5-dihydro-4-(2,5-difluorophenyl)-2-methoxycarbonylaminoimidazole;

4,5-dihydro-4-(2,4-difluorophenyl)-2-methoxycarbonylaminoimidazole;

4,5-dihydro-4-(2,3-difluorophenyl)-2-methoxycarbonylaminoimidazole;

4,5-dihydro-4-(3,4-difluorophenyl)-2-methoxycarbonylaminoimidazole;

4,5-dihydro-4-(3,5-difluorophenyl)-2-methoxycarbonylaminoimidazole;

4,5-dihydro-4-(2-fluorophenyl)-2-methoxycarbonylaminoimidazole;

4,5-dihydro-4-(3-fluorophenyl)-2-methoxycarbonylaminoimidazole;

4,5-dihydro-4-(4-fluorophenyl)-2-methoxycarbonylaminoimidazole;

4-(2,6-dichlorophenyl)-4,5-dihydro-2-methoxycarbonylaminoimidazole;

4-(2,5-dichlorophenyl)-4,5-dihydro-2-methoxycarbonylaminioimidazole;

4-(2,4-dichlorophenyl)-4,5-dihydro-2-methoxycarbonylaminoimidazole;

4-(2,3-dichlorophenyl)-4,5-dihydro-2-methoxycarbonylaminoimidazole;

4-(2-chlorophenyl)-4,5-dihydro-2-methoxycarbonylaminoimidazole;

4-(3-chlorophenyl)-4,5-dihydro-2-methoxycarbonylaminoimidazole;

4-(4-chlorophenyl)-4,5-dihydro-2-methoxycarbonylaminoimidazole;

4-(2,6-dibromophenyl)-4,5-dihydro-2-methoxycarbonylaminoimidazole;

4-(2-bromophenyl)-4,5-dihydro-2-methoxycarbonylaminoimidazole;

4-(3-bromophenyl)-4,5-dihydro-2-methoxycarbonylaminoimidazole;

2-ethoxycarbonylamino-4,5-dihydro-4-(2,6-difluorophenyl)-imidazole;

4,5-dihydro-4-(4-hydroxyphenyl)-2-methoxycarbonylaminoimidazole;

4-(2,5-dibromophenyl)-4,5-dihydro-2-methoxycarbonylaminoimidazole;

4-(2,3-dibromophenyl)-4,5-dihydro-2-methoxycarbonylaminoimidazole;

4,5-dihydro-4-(2,6-diiodophenyl)-2-methoxycarbonylaminoimidazole;

4,5-dihydro-4-(2-iodophenyl)-2-methoxycarbonylaminoimidazole;

4,5-dihydro-2-methoxycarbonylamino-4-(2-methylphenyl)-imidazole;

4,5-dihydro-2-methoxycarbonylamino-4-(3-methylphenyl)-imidazole;

4,5-dihydro-2-methoxycarbonylamino-4-(2,6-dimethoxyphenyl)-imidazole;

4,5-dihydro-2-methoxycarbonylamino-4-(2,5-dimethoxyphenyl)-imidazole;

4,5-dihydro-2-methoxycarbonylamino-4-(2,4-dimethoxyphenyl)-imidazole;

4,5-dihydro-2-methoxycarbonylamino-4-(2,3-dimethoxyphenyl)-imidazole;

4,5-dihydro-2-methoxycarbonylamino-4-(2-methoxyphenyl)-imidazole; and 4,5-dihydro-2-methoxycarbonylamino-4-(2,6-diethoxyphenyl)-imidazole;
2-ethoxycarbonylamino-4-(2,4-difluorophenyl)-4,5-dihydroimidazole;
2-ethoxycarbonylamino-4,5-dihydro-(2,6-dihydroxyphenyl)-imidazole;
2-ethoxycarbonylamino-4,5-dihydro-4-(2,6-dimethoxyphenyl)-imidazole; and
4-(3-chlorophenyl)-4,5-dihydro-2-isopropoxycarbonylaminoimidazole.

Certain of the compounds of this invention are useful as anti-convulsants or anti-epileptics, particularly compounds represented by formula (I), wherein
 (a) R is methyl or ethyl and $R^1$ and $R^2$ are independently chosen from hydrogen and fluoro;
 (b) R is methyl, $R^1$ is hydrogen and $R^2$ is ethyl, chloro, 2-bromo, 3-bromo, 2-methyl and 3-methyl; and
 (c) R is methyl, and $R^1$ and $R^2$ together are 2,3-, 2,4-, 2,5-, or 3,5-dimethyl.

Representative compounds include, in addition to those applicable compounds named above,
4,5-dihydro-2-methoxycarbonylamino-4-(2,5-dimethylphenyl)-imidazole;
4,5-dihydro-2-methoxycarbonylamino-4-(2,4-dimethylphenyl)-imidazole;
4,5-dihydro-2-methoxycarbonylamino-4-(2,3-dimethylphenyl)-imidazole;
4,5-dihydro-2-methoxycarbonylamino-4-(3,5-dimethylphenyl)-imidazole;
4,5-dihydro-4-(2-ethylphenyl)-2-methoxycarbonylaminoimidazole;
4,5-dihydro-4-(3-ethylphenyl)-2-methoxycarbonylaminoimidazole; and
4,5-dihydro-4-(4-ethylphenyl)-2-methoxycarbonylaminoimidazole.

Other compounds of this invention have activity as centrally acting skeletal muscle relaxants particularly those compounds represented by formula (I), wherein
 (a) R is methyl, $R^1$ is hydrogen and $R^2$ is fluoro, chloro, alkoxy of two through six carbon atoms, alkyl of one through six carbon atoms, trifluoromethyl, 3-methoxy, 2-iodo or 4-methoxy;
 (b) R is methyl and $R^1$ and $R^2$ together are dialkoxy of two through six carbon atoms (preferably at the 2,4- or 2,6-position), dichloro, 2,6-dibromo, and 3,5-dimethyl;
 (c) R is ethyl, $R^1$ and $R^2$ together are dihydroxy, difluoro, dichloro, dimethyl or dimethoxy;
 (d) R is methyl and $R^1$ and $R^2$ together are 3,4-methylenedioxy; and
 (e) R is alkyl of 2-3 carbons and $R^1$ and $R^2$ are both hydrogen and the pharmaceutically acceptable salts thereof.

Representative compounds having centrally induced skeletal muscle relaxant activity which are useful to reduce or palliate centrally induced muscle spasms, in mammals, and prophylactically to prevent or reduce the frequency or intensity of such spasms, include, aside from those pertinent compounds listed above, the following:
4,5-dihydro-4-(2-isopropylphenyl)-2-methoxycarbonylaminoimidazole;
4,5-dihydro-4-(3-propylphenyl)-2-methoxycarbonylaminoimidazole;
4,5-dihydro-4-(4-propylphenyl)-2-methoxycarbonylaminoimidazole;
4,5-dihydro-4-(4-n-hexylphenyl)-2-methoxycarbonylaminoimidazole;
4,5-dihydro-2-methoxycarbonylamino-4-(2-trifluoromethylphenyl)imidazole;
4,5-dihydro-2-methoxycarbonylamino-4-(3-trifluoromethylphenyl)imidazole;
4,5-dihydro-2-methoxycarbonylamino-4-(4-trifluoromethylphenyl)imidazole;
4-(2,5-diethoxyphenyl)-4,5-dihydro-2-methoxycarbonylaminoimidazole;
4-(2,4-diethoxyphenyl)-4,5-dihydro-2-methoxycarbonylaminoimidazole;
4-(2-ethoxyphenyl)-4,5-dihydro-2-methoxycarbonylaminoimidazole;
4-(4-ethoxyphenyl)-4,5-dihydro-2-methoxycarbonylaminoimidazole;
4,5-dihydro-2-methoxycarbonylamino-4-(2,4-[di-n-propoxy]-phenyl)-imidazole;
4,5-dihydro-2-methoxycarbonylamino-4-(2,6-diisopropoxyphenyl)-imidazole;
4-(2-n-butoxyphenyl)-4,5-dihydro-2-methoxycarbonylaminoimidazole;
4,5-dihydro-2-methoxycarbonylamino-4-(3-methoxyphenyl)-imidazole;
4,5-dihydro-2-methoxycarbonylamino-4-(3,4-methylenedioxy)-imidazole;
4,5-dihydro-2-methoxycarbonylamino-4-(4-methylphenyl)-imidazole;
4,5-dihydro-2-ethoxycarbonylamino-4-(4-isopropylphenyl)-imidazole;
4,5-dihydro-4-(4-isobutoxyphenyl)-2-methoxycarbonylaminoimidazole;
4,5-dihydro-2-methoxycarbonylamino-4-(2,4-n-pentyloxyphenyl)-imidazole;
4,5-dihydro-4-(2,6-n-hexyloxyphenyl)-methoxycarbonylaminoimidazole;
4,5-dihydro-4-(2-isopentyloxyphenyl)-methoxycarbonylaminoimidazole; and
4,5-dihydro-4-(4-n-hexyloxyphenyl)-2-methoxycarbonylaminoimidazole.

Certain of the compounds of this invention produce a neuroleptic effect (i.e. tranquilizing, sedative, hypnotic, etc.) in mammals and thus are useful for treating, e.g., anxiety. These include compounds chosen from those represented by formula (I) wherein
 (a) R is methyl, $R^1$ is hydrogen and $R^2$ is 2- or 3-methyl, 2- or 3-ethyl, 2-iodo, 3-fluoro, 2-ethoxy or 3-methoxy;
 (b) R is methyl, $R^1$ is iodo, ethyl, isopropoxy, n-propoxy or ethoxy at the 2-position of the phenyl ring and $R^2$ is the same as $R^1$ at any other position on the phenyl ring; and
 (c) R is methyl, $R^1$ and $R^2$ together are 2,6-, 2,5-, or 2,3-dibromo; 2,3- or 2,5-dichloro; 2,6-, 3,5- or 2,3-dimethyl; or 2,3- or 2,5-dimethoxy;
 (d) R is ethyl, $R^1$ is hydrogen and $R^2$ is 2-iodo or 2-ethyl; or
 (e) R is ethyl and $R^1$ and $R^2$ together are 2,6-, 2,5- or 2,3-diethyl, 2,5- or 2,3-diethoxy, difluoro, dimethyl, dimethoxy, dihydroxy or dichloro and the pharmaceutical salts thereof.

Representative compounds, aside from the pertinent compounds named hereinabove, include
4,5-dihydro-4-(2,5-diiodophenyl)-2-methoxycarbonylaminoimidazole;
4,5-dihydro-4-(2,4-diiodophenyl)-2-methoxycarbonylaminoimidazole;
4,5-dihydro-4-(2,3-diiodophenyl)-2-methoxycarbonylaminoimidazole;

4,5-dihydro-4-(2,6-diethylphenyl)-2-methoxycarbonylaminoimidazole;
4,5-dihydro-4-(2,5-diethylphenyl)-2-methoxycarbonylaminoimidazole;
4,5-dihydro-4-(2,4-diethylphenyl)-2-methoxycarbonylaminoimidazole;
4,5-dihydro-4-(2,3-diethylphenyl)-2-methoxycarbonylaminoimidazole;
4,5-dihydro-2-methoxycarbonylamino-4-(2,6-di[n-propyl]-phenyl)-imidazole;
4,5-dihydro-2-methoxycarbonylamino-4-(2,4-diisopropylphenyl)-imidazole;
4,5-dihydro-2-methoxycarbonylamino-4-(2,5-diisopropylphenyl)-imidazole;
4,5-dihydro-2-methoxycarbonylamino-4-(2,3-diisopropylphenyl)-imidazole;
4,5-dihydro-2-methoxycarbonylamino-4-(2,5-diisopropoxyphenyl)-imidazole;
4,5-dihydro-2-methoxycarbonylamino-4-(2,3-di[n-propoxy]-phenyl)-imidazole;
4,5-dihydro-2-methoxycarbonylamino-4-(2-n-propoylphenyl)-imidazole;
4,5-dihydro-4-(2,5-diethoxyphenyl)-2-methoxycarbonylaminoimidazole;
4,5-dihydro-4-(2-ethoxyphenyl)-2-methoxycarbonylaminoimidazole;
4,5-dihydro-4-(2,3-diethoxyphenyl)-2-methoxycarbonylaminoimidazole;
4,5-dihydro-2-methoxycarbonylamino-4-(2-methoxyphenyl)-imidazole;
4,5-dihydro-4-(2-iodophenyl)-2-ethoxycarbonylaminoimidazole;
4,5-dihydro-4-(2,6-diethylphenyl)-2-ethoxycarbonylaminoimidazole;
4,5-dihydro-4-(2,5-diethylphenyl)-2-ethoxycarbonylaminoimidazole;
4,5-dihydro-4-(2,3-diethylphenyl)-2-ethoxycarbonylaminoimidazole;
4,5-dihydro-4-(2-ethylphenyl)-2-ethoxycarbonylaminoimidazole;
4,5-dihydro-4-(2,5-ethoxyphenyl)-2-ethoxycarbonylaminoimidazole; and
4,5-dihydro-4-(2,3-ethoxyphenyl)-2-ethoxycarbonylaminoimidazole.

As will be appreciated from the above discussion, a number of the compounds exhibit a mixed spectrum of activities and thus one compound may have more than one utility. Such a mixed spectrum of activities is now recognized to be especially desirable in treating some psychotropic disorders, since such such disorders are seldom a pure phenomenon or symptoms. For example, based on small animal tests, 4,5-dihydro-4-(3-fluorophenyl)-2-methoxycarbonylaminoimidazole and 4,5-dihydro-2-methoxycarbonylamino-4-(2-methylphenyl)-imidazole exhibit a desirable combination of potent antidepressant activity and moderate to mild depressant activity, and in addition also exhibit some anticonvulsant activity. 4-(2,6-Dichlorophenyl)-4,5-dihydro-2-methoxycarbonylaminoimidazole, on the other hand, exhibits potent antidepressant activity but is without appreciable depressant activity.

Administration and Formulation

As stated previously, the compounds of this invention are administered to mammals to treat, palliate or prevent abnormal conditions related to the central nervous system such as depressive illness, epileptic or convulsant seizure states and other neurological disorders, anxiety, as well as certain disorders involving muscle spasms or spasticity.

In general, the preferred dosage depends upon the particular subject and disorder being treated and can vary within wide limits such as, for example, between 0.01 and 200 mg per kg of body weight per day. Generally, where the compounds are administered as antidepressants, they can be administered in the same manner as imipramine, preferably at the rate of less than 40 mg/kg per day and even more preferably less than 20 mg/kg per day. Where the compounds are administered as anticonvulsants, they are best administered prophylactically to prevent or reduce the occurrence and/or severity of convulsions in mammals which are subject to convulsions which are etiopathic to the central nervous system, preferably at a rate less than 100 mg/kg per day.

When used as a depressant, to treat anxiety, for example, they are administered orally to reduce anxiety, preferably at less than 100 mg/kg per day. When used as a muscle relaxant they are best administered orally, preferably at a rate of less than 100 mg/kg per day.

The compounds can be administered orally, rectally or parenterally (for example, by intravenous, intraperitoneally or intramuscular injection). Where the compounds are administered parenterally, they will, of course, be administered in liquid dosage forms, whereas when administered orally or rectally, they can be administered in both solid and liquid forms. Typically, the dosage forms comprise the compounds in a pharmaceutically acceptable carrier, preferably formulated in unit dosage form to facilitate the simple administration of precise dosages. The dosage form can optionally contain other compatible medicaments and preservatives, emulsifying agents and wetting agents and buffering agents. Liquid dosage forms include, for example, solutions, suspensions, emulsions, syrups, elixirs, etc. Liquid carriers include, for example, water, saline solution, etc. Solid dosage forms include, for example, tablets, powders, capsules, pills, etc. Suitable solid carriers include, for example, pharmaceutical grades of starch, lactose, sodium saccharine, sodium bisulfite and the like, and conventional suppository carriers, e.g. polyethylene glycol, polysorbate, stearic acid, diglycol stearate, etc.

The Process

The preferred process, of the invention, can be represented by the following overall reaction equation:

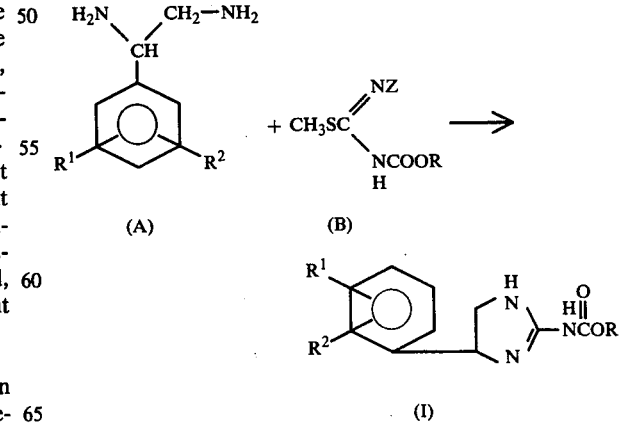

wherein R, $R^1$ and $R^2$ are as defined hereinabove, and Z is hydrogen or the same as the group —COOR.

This reaction can be conveniently effected by treating the compound of formula A, having the desired $R^1$ and $R^2$ substituent, or typically an acid salt thereof, e.g. the dihydrochloride salt, with the starting material of formula B having the desired R substituent, in a suitable solvent. Typically, the reaction is conducted under alkaline to slightly acid conditions, preferably essentially neutral. Typically, where an acid salt of formula A is used, a sufficient amount of an inorganic or organic base is added to the reaction mixture either before or after the addition of one or both of the reactants to neutralize all or part of the acid salt moiety. Suitable bases which can be used include, for example, alkali metal carbonates, bicarbonates or acetates (for example, sodium carbonate, potassium carbonate, sodium bicarbonate, sodium acetate), alkali metal lower alkoxides, (for example, sodium methoxide, potassium methoxide, sodium butoxide, lithium methoxide, and the like), alkali metal and alkaline earth metal hydroxides (for example, sodium hydroxide, potassium hydroxide, calcium hydroxide, and the like), and mixtures thereof. Suitable organic bases include, for example, pyridine, triethylamine, diazabicyclononane, and the like or mixtures thereof. Conveniently, the solvent is a mixture of water and one or more inert organic solvents. Suitable inert organic solvents which can be used include, for example, methanol, ethanol, isopropanol, diethyl ether, chloroform, benzene and the like and mixtures thereof. Typically, the reaction is carried out at temperatures in the range of about from 10° to 100° C., preferably at about from 15° to 35° C., for about from ½ hour to 14 days. Typically, a mole ratio of about from 0.5 to 2, preferably about 1 mole of starting material A is used per mole of starting material B. However, temperatures, reaction times, and mole ratios both above and below these ranges can be used. Optimum conditions will, of course, vary with the particular reactants and solvents, and can be determined by routine experimentation. The products of formula I can be separated from the product reaction mixture and further purified by conventional procedures, e.g. filtration, washing, evaporation, crystallization and the like. Non-limiting illustrations of detailed separation and purification procedures can be had by reference to the Examples set forth hereinbelow.

The starting materials of formula B are known compounds and can be prepared according to known procedures or, for example, by the procedure described in Example 9 hereinbelow or by obvious modifications of such procedures. The compounds of formula B can be used either as the respective mono- (Z is H) or bis- (Z is COOR) or as a mixture of the mono- and bis- compounds. Conveniently, the compound of formula B is prepared as a mixture of the mono- (Z is H) and bis- (Z is COOR) and the mixture then used in the aforedescribed reaction without separation of the mono- and bis- products. The starting materials of formula A are also generally known compounds and can be prepared according to known procedures, note, for example, the procedures described by W. L. Matier et al in the *Journal of Medicinal Chemistry*, Vol. 16, No. 8, page 901 (1973) and by the procedures described herein in the Preparations, or by obvious modifications of such procedures.

In a further process embodiment, the compounds of the invention can be prepared by the following overall reaction equation.

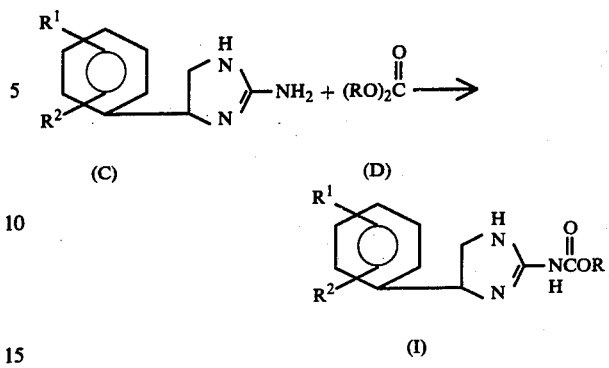

wherein R, $R^1$ and $R^2$ are as defined hereinabove.

This reaction can be conveniently effected by treating the compound of formula C, having the desired $R^1$ and $R^2$ substituent, or typically an acid salt thereof, e.g. the hydrobromide salt, with the starting material of formula D having the desired R substituent in an inert solvent or by using an excess of compound D as the solvent. Typically where an acid salt of compound C is used as the starting material, the salt is treated before addition of compound D with a sufficient amount of an inorganic or organic base to liberate the free base. Suitable bases which can be used include, for example, alkali metal carbonates, alkali metal lower alkoxides (for example, sodium methoxide, potassium methoxide, sodium t-butoxide, lithium methoxide, and the like), alkali metal and alkaline earth metal hydroxides (for example, sodium hydroxide, potassium hydroxide, calcium hydroxide, and the like), and mixtures thereof. Suitable organic bases include, for example, pyridine, triethylamine, diazabicyclononane, and the like of mixtures thereof. Suitable inert organic solvents which can be used include, for example, toluene, dioxane, and the like and mixtures thereof.

The compounds of the invention can also be prepared by reacting the compound of formula C, having the desired $R^1$ and $R^2$ substituents with an alkyl chloroformate (ClCOOR) having the desired R-alkyl substituent in a suitable organic solvent; e.g. acetone.

The starting materials of formula C are also known compounds and can be prepared according to known procedures such as, for example, described by Matier et al in the *Journal of Medicinal Chemistry*, Vol. 16, No. 8, page 901 (1973) and the Preparations set forth hereinbelow or obvious modifications of such procedures.

The respective optically active isomers of formula I can be conveniently prepared by using the corresponding optically active isomer starting material of formula A or C in the afore-described processes. The optically active isomer starting materials can be obtained by resolution of the corresponding (dl) mixture by applying conventional resolution procedures, note, for example, the procedure described in *Ann. Chem.*, Vol. 494, page 143 (1932).

The pharmaceutically acceptable salts of the invention can be conveniently prepared by treating the corresponding free base of formula I, of the invention, with an acid or via other conventional procedures such as, for example, ion exchange.

A further understanding of the invention can be had from the following non-limiting Preparations and Examples, wherein, unless expressly stated to the contrary, racemates are used as starting materials and correspondingly racemic mixtures are obtained as products.

PREPARATION 1

This preparation illustrates a method of preparing certain β-amino-β-phenyl (or substituted phenyl)-ethylamines. About 145 ml. of concentrated hydrochloric acid is diluted with 500 ml. of water and 180 g. of benzylamine is dissolved in this acid. The solution is cooled in an ice bath under stirring and 250 g. of sodium cyanide in three portions. The reaction temperature was not allowed to rise above 35° C., and was finally stirred at room temperature overnight. The organic materials were extracted into benzene and the benzene layer was separated from the aqueous layer. The benzene is removed under reduced pressure and the residual oil is dissolved in a mixture of 1.5 l. of ether and 1.5 l. of isopropanol. From this solution the crude hydrochloride salt (400 g.) of α-benzylamino-4-isopropylphenylacetonitrile is precipitated by addition of 150 ml. of concentrated hydrochloric acid. This crude material is then dissolved in 4 l. of warm ethanol, and the ethanolic solution is concentrated under reduced pressure, to 1.5 l. affording 166 g. of the hydrochloride salt of α-benzylamino-(4-isopropylphenyl)-acetonitrile, m.p. 133°–136° C. The free amine is liberated from the salt by addition of dilute aqueous sodium hydroxide and is extracted into benzene. The benzene solution is dried over potassium carbonate, filtered and the solvent is removed under reduced pressure. The remaining oily residue is dissolved in about 500 ml. of ether and this solution is admixed to an externally cooled (ice-methanol bath) of 41 g. of lithium aluminum hydride in 1 l. of ether. The mixture is then allowed to warm to room temperature and is stirred overnight (about 16 hours). The mixture is then worked up by successive, dropwise addition of 1) 40 ml. of water, 2) 42 ml. of 15% wt., aqueous sodium hydroxide, and 3) 75 ml. of water. The solid inorganic material is removed by filtration and a mixture of 120 ml. of concentrated hydrochloric acid and 300 ml of isopropanol is added to the filtrate resulting in the precipitation of β-benzylamino-β-(4-isopropylphenyl)-ethylamine as its dihydrochloride salt which is then collected by filtration and dried under vacuum affording 67 g., m.p. 240°–243° C.

The 67 g. of β-benzylamino-β-(4-isopropylphenyl)-ethylamine dihydrochloride is dissolved in 250 ml. of water and this solution is combined first with a slurry of 3 g. of 5%, by wt., palladium in charcoal in a few milliliters of water, and then with 200 ml. of methanol. This mixture is hydrogenated at atmospheric pressure. After an amount of hydrogen stoichiometrically equivalent to the amount required to replace the benzyl group with hydrogen is consumed, the hydrogenolysis is discontinued and the palladium on charcoal catalyst is removed by filtration. The filtrate is concentrated to dryness and the solid residue is triturated with ether, collected and dried under vacuum, affording 42.5 g. of β-amino-β-(4-isopropylphenyl)-ethylamine, dihydrochloride, m.p. 286°–288° C.

Similarly, by following the same procedure but using the corresponding benzaldehyde or substituted benzaldehyde as starting material in place of 4-isopropylbenzaldehyde, the dihydrochloride salts of the following compounds are respectively prepared.

β-amino-β-phenethylamine; m.p. 308°–310° C.;
β-amino-β-(4-methylphenyl)-ethylamine; m.p. 318°–319° C.;
β-amino-β-(2-methylphenyl)-ethylamine; m.p. 281°–287° C.;
β-amino-β-(3-methylphenyl)-ethylamine; m.p. 281°–287° C.;
β-amino-β-(2-ethylphenyl)-ethylamine;
β-amino-β-(3-ethylphenyl)-ethylamine;
β-amino-β-(4-ethylphenyl)-ethylamine;
β-amino-β-(4-t-butylphenyl)-ethylamine;
β-amino-β-(2-t-butylphenyl)-ethylamine;
β-amino-β-(4-hexylphenyl)-ethylamine; m.p. 215°–230° C.;
β-amino-β-(3-hexylphenyl)-ethylamine;
β-amino-β-(4-methoxyphenyl)-ethylamine;
β-amino-β-(3-methoxyphenyl)-ethylamine; m.p. 250°–254° C.;
β-amino-β-(2-methoxyphenyl)-ethylamine;
β-amino-β-(2-ethoxyphenyl)-ethylamine; m.p. 198°–200° C.;
β-amino-β-(3-ethoxyphenyl)-ethylamine;
β-amino-β-(4-ethoxyphenyl)-ethylamine;
β-amino-β-(4-isopropoxyphenyl)-ethylamine;
β-amino-β-(3-t-butoxyphenyl)-ethylamine;
β-amino-β-(3-pentoxyphenyl)-ethylamine;
β-amino-β-(4-fluorophenyl)-ethylamine;
β-amino-β-(3-fluorophenyl)-ethylamine; m.p. 280°–285° C.;
β-amino-β-(2-fluorophenyl)-ethylamine; m.p. 260°–263° C.;
β-amino-β-(4-trifluoromethylphenyl)-ethylamine; m.p. 245°–255° C.;
β-amino-β-(2-trifluoromethylphenyl)-ethylamine;
β-amino-β-(3-trifluoromethylphenyl)-ethylamine;
β-amino-β-(2,3-dimethylphenyl)-ethylamine;
β-amino-β-(2,4-dimethylphenyl)-ethylamine;
β-amino-β-(2,5-dimethylphenyl)-ethylamine; m.p. 332°–334° C.;
β-amino-β-(2,6-dimethylphenyl)-ethylamine;
β-amino-β-(3,4-dimethylphenyl)-ethylamine;
β-amino-β-(3,5-dimethylphenyl)-ethylamine;
β-amino-β-(3,4-di-t-butylphenyl)-ethylamine;
β-amino-β-(2,6-di-t-butylphenyl)-ethylamine;
β-amino-β-(3,5-di-t-butylphenyl)-ethylamine;
β-amino-β-(2,5-di-n-hexylphenyl)-ethylamine;
β-amino-β-(2,4-di-n-hexylphenyl)-ethylamine;
β-amino-β-(3,4-di-n-hexylphenyl)-ethylamine;
β-amino-β-(2,4-dimethoxyphenyl)-ethylamine;
β-amino-β-(2,3-dimethoxyphenyl)-ethylamine;
β-amino-β-(2,5-dimethoxyphenyl)-ethylamine;
β-amino-β-(2,6-dimethoxyphenyl)-ethylamine;
β-amino-β-(3,5-dimethoxyphenyl)-ethylamine; m.p. 291°–294° C.;
β-amino-β-(2,5-diisopropoxyphenyl)-ethylamine;
β-amino-β-(2,4-diisopropoxyphenyl)-ethylamine;
β-amino-β-(3,4-diisopropoxyphenyl)-ethylamine;
β-amino-β-(2,6-di-n-hexoxyphenyl)-ethylamine;
β-amino-β-(3,4-di-n-hexoxyphenyl)-ethylamine;
β-amino-β-(3,5-di-n-hexoxyphenyl)-ethylamine;
β-amino-β-(2,3-difluorophenyl)-ethylamine;
β-amino-β-(2,4-difluorophenyl)-ethylamine;
β-amino-β-(2,5-difluorophenyl)-ethylamine; m.p. 298°–302° C.;
β-amino-β-(2,6-difluorophenyl)-ethylamine;
β-amino-β-(3,4-difluorophenyl)-ethylamine;
β-amino-β-(3,5-difluorophenyl)-ethylamine

PREPARATION 2

This preparation illustrates a method of preparing β-amino-β-(3,4-methylenedioxyphenyl) ethylamine. In this example 51 g. of 3,4-methylenedioxybenzaldehyde is stirred for 16 hours in a slurry of 32 g. of sodium cyanide and 35 g. of ammonium chloride in 130 ml. of dimethylsulfoxide and 30 ml. of water. The resulting mixture is diluted with water and then extracted with benzene. The benzene extract is washed with water and then extracted into 1N aqueous hydrochloric acid. The acidic solution is first washed with ether and then made alkaline by addition of 10%, wt., aqueous sodium hydroxide. The product is extracted into benzene. When the benzene is evaporated, there is 28 g. of oily α-amino-(3,4-methylenedioxyphenyl) acetonitrile. Scratching of this material under hexane causes solidification of this product, m.p. 41°–43.5° C.

A solution containing 28 g. of α-amino-(3,4-methylenedioxyphenyl)acetonitrile in 100 ml. of ethyl ether is prepared, and then added to a stirred solution of 14 g. of lithium aluminum hydride in 400 ml. of ether. During this addition, the temperature of the mixture is kept at 0° C. Stirring is continued while the reaction mixture is allowed to warm to room temperature. After 15-20 hours, the mixture is worked up by successive, dropwise addition of (1) 15 ml. of water, (2) 15 ml. of 15% aqueous sodium hydroxide, and (3) 28 ml. of water. This mixture is stirred until the solid is observed to change color from greenish-gray to near-white. The solid is first removed by filtration and the β-amino-β-(3,4-methylenedioxyphenyl)-ethylamine is precipitated from the filtrate as its dihydrochloride salt by addition of 200 ml. of ethyl ether containing 14 g. of hydrogen chloride. The precipitate is collected by filtration and dried, under vacuum, m.p. 265°–268° C.

By following in principle the same procedure of this preparation, but using other appropriate benzaldehydes in place of 3,4-methylenedioxy benzaldehyde, the products prepared in Preparation 1 are respectively prepared.

PREPARATION 3

This preparation illustrates further methods of preparing β-amino-β-(phenyl or substituted phenyl)-ethylamine and salts via the β-benzylamino-β-(phenyl or substituted phenyl)-ethylamine intermediate. In this example, 22 g. of benzylamine is dissolved in 50 ml. of water and 17 ml. of concentrated hydrochloric acid. The solution is cooled to about 0° C., in an ice-bath, and added to it first is 25 g. of 3-fluorobenzaldehyde and then 10 g. of sodium cyanide. This mixture is then stirred for 17 hours at room temperature and then extracted with benzene. The organic and water phase layers are separated and the organic (benzene) layer is first washed with water and then shaken with ~10%, wt., aqueous hydrochloric acid affording a crystalline precipitate of the hydrochloride salt of α-N-benzylamino-(3-fluorophenyl)acetonitrile. This intermediate produce is collected and dried under vacuum (36 g., m.p. 166°–169° C.). The free amine is liberated from the salt by the addition of diluted aqueous sodium hydroxide and is then extracted into benzene. The benzene solution is dried over potassium carbonate, filtered, and concentrated by evaporation affording an oily residue which is then dissolved in 80 ml. of ethyl ether. This solution is slowly admixed over a 2 hour period to an externally cooled (methanol-ice bath) solution of 10 g. of lithium aluminum hydride in 200 ml. of ethyl ether. The mixture is allowed to warm to room temperature and stirred for about 16 hours at room temperature. The mixture is then worked up by successive, dropwise addition (with constant stirring) of (1) 10 ml. of water; (2) 10 ml. of 15%, wt., aqueous sodium hydroxide, and (3) 19 ml. of water. It is filtered to remove solid inorganic materials. 25 Ml. of concentrated hydrochloric acid and 200 ml. of ethanol is added to the filtrate resulting in precipitation of the dihydrochloride salt of β-benzylamino-β-(3-fluorophenyl)-ethylamine which is then collected by filtration and dried under vacuum affording 22 g. of this product, m.p. 238°–241° C.

The 22 g. of the above product, dihydrochloride salt, is added to a slurry containing 1 g. of 5%, by wt., palladium on charcoal in 250 ml. of water, and 250 ml. of ethanol and then hydrogenated at atmospheric pressure. After an amount of hydrogen stoichiometrically equivalent to the amount required to replace the benzyl group with hydrogen is consumed, the hydrogenolysis is discontinued and the palladium on charcoal catalyst removed by filtration. The filtrate is concentratd to dryness by evaporation and then refluxed with about 250 ml. of isopropanol for about ½ hour. The slurry is then cooled, filtered, and the collected solid is dried, under vacuum, affording 10 g. of crude β-amino-β-(3-fluorophenyl)-ethylamine dihydrochloride salt, m.p. 280°–285° C.

Similarly, by following the same procedure using the corresponding benzaldehydes in place of m-fluorobenzaldehyde as starting materials, the compounds prepared in Preparation 1 are respectively prepared.

PREPARATION 4

This preparation illustrates a method which is particularly useful for preparing β-amino-β-(chloro-, bromo- or iodo-substituted phenyl)ethylamine intermediate.

In this example, a solution of 9.2 g. (58 m. mole) of N,N-dichlorourethane (DCU) in about 30 ml. of benzene is stirred at ice-bath temperature (0°–10° C.) and 10 g. (58 m. mole) of 2,6-dichlorostyrene is added dropwise. The mixture is then stirred at room temperature for 2 days. To this mixture is then added an excess of aqueous sodium disulfite solution and stirring is continued for 16 hours. The layers are separated and the organic (upper) layer is washed with aqueous sodium bicarbonate, dried over potassium carbonate, filtered and concentrated in vacuo. There is 12 g. of oily residue containing the reaction product 1-ethoxycarbonylamino-2-chloro-2-(2,6-dichlorophenyl)ethane as well as some unreacted 2,6-dichlorostyrene. This oily residue is dissolved in 150 ml. of dimethylformamide, potassium phthalimide (22 g.; 119 m. mole) is added and the mixture is stirred in an oil bath at 75° for 3 days and an additional day at 110°. It is poured into ice-water and extracted with benzene. The benzene extract is washed several times with 5% sodium hydroxide solution, the solvent is removed and the residue is stirred with 100 ml. of refluxing 20% hydrochloric acid for 2 days. The acidic mixture is cooled to room temperature, washed with ether and is then concentrated to dryness. The solid residue is triturated and the insoluble solid is collected and dried, to give 3.7 g. of β-amino-β-2,6-dichlorophenylethylamine as its dihydrochloride salt, m.p. 334°–336° (with decomposition).

Similarly, by following in principle the procedure set forth in this preparation but substituting other appropriate mono- or di-chloro-, bromo- or iodo-styrenes for 2,6-dichloro-styrene the following representative compounds are prepared:

β-amino-β-(2-chlorophenyl)-ethylamine; m.p. 297°–303° C.;

β-amino-β-(4-chlorophenyl)-ethylamine; m.p. 292°–294° C.;
β-amino-β-(3-chlorophenyl)-ethylamine; m.p. 286°–289° C.;
β-amino-β-(2-bromophenyl)-ethylamine; m.p. 295°–299° C.;
β-amino-β-(4-bromophenyl)-ethylamine;
β-amino-β-(3-iodophenyl)-ethylamine;
β-amino-β-(4-iodophenyl)-ethylamine;
β-amino-β-(2,3-dichlorophenyl)-ethylamine;
β-amino-β-(2,5-dichlorophenyl)-ethylamine;
β-amino-β-(3-bromophenyl)-ethylamine, m.p. 284°–290° C.;
β-amino-β-(2,6-dibromophenyl)-ethylamine; and
β-amino-β-(2,6-diiodophenyl)-ethylamine.

This preparation is also useful for preparing β-amino-β-(trifluoromethylphenyl)-ethylamines and certain β-amino-β-(2,6-disubstituted phenyl)-ethylamines.

EXAMPLE 1

This example illustrates methods according to the invention of preparing the compounds of the invention. In this example, 50 ml. of isopropanol and 2.15 g. of sodium methoxide is added to a solution containing 5.02 g. of the dihydrochloride salt of β-amino-β-(4-isopropylphenyl)-ethylamine dissolved in 25 ml. of water. The mixture is stirred for 15 minutes and then a solution containing 4.12 g. of a mixture of 1-mono- and 1,3-bis-(methoxycarbonyl)-S-methylisothiourea in 50 ml. of chloroform is added and then stirred for about 2 weeks at room temperature. The mixture is then concentrated by evaporation to near dryness and the solid residue is swirled with water, collected, and stirred in 25 ml. of aqueous 1 Normal hydrochloric acid for 1 hour. The resulting mixture is washed with ethyl ether, then treated with aqueous sodium bicarbonate and filtered. The collected solid is then stirred with distilled water, refiltered and washed in this manner three more times, then dried overnight at room temperature affording 4.94 g. of crude product, m.p. 212°–215° C. The crude product is then purified by recrystallization from isopropanol affording 3.29 g. of 4,5-dihydro-4-(4-isopropylphenyl)-2-methoxycarbonylamino-imidazole, m.p. 213°–215° C.

Similarly, by following the same procedure but using the corresponding substituted phenyl or unsubstituted phenyl β-amino-ethylamine starting materials in place of β-amino-β-(4-isopropylphenyl)-ethylamine, the following compounds are respectively prepared:
4,5-dihydro-2-methoxycarbonylamino-4-phenylimidazole; m.p. 209°–210° C.;
4,5-dihydro-2-methoxycarbonylamino-4-(4-methylphenyl)-imidazole; m.p. 205°–207° C.;
4,5-dihydro-2-methoxycarbonylamino-4-(2-methylphenyl)-imidazole; m.p. 218°–219° C.;
4,5-dihydro-2-methoxycarbonylamino-4-(3-methylphenyl)-imidazole; m.p. 182°–183.5° C.;
4,5-dihydro-4-(3-ethylphenyl)-2-methoxycarbonylaminoimidazole;
4,5-dihydro-4-(4-ethylphenyl)-2-methoxycarbonylaminoimidazole;
4-(4-t-butylphenyl)-4,5-dihydro-2-methoxycarbonylaminoimidazole;
4-(2-t-butylphenyl)-4,5-dihydro-4-methoxycarbonylaminoimidazole;
4,5-dihydro-4-(2-n-hexylphenyl)-2-methoxycarbonylaminoimidazole;
4,5-dihydro-4-(3-n-hexylphenyl)-2-methoxycarbonylaminoimidazole; and
4,5-dihydro-2-methoxycarbonylamino-4-(4-n-hexylphenyl)-imidazole; m.p. 188°–189° C.

Similarly, by following the same procedure but respectively replacing the 1-mono-1,3-bis(methoxycarbonyl)-S-methyl-isothiourea mixture with the following mixtures 1-mono and 1,3-bis(ethoxycarbonyl)-S-methylisothiourea; 1-mono and 1,3-bis(isopropoxycarbonyl)-S-methylisothiourea; and 1-mono-1,3-bis(n-pentoxycarbonyl)-S-methylisothiourea, the corresponding 2-ethoxycarbonylamino (e.g. 4,5-dihydro-2-ethoxycarbonylamino-4-(4-isopropylphenyl)-imidazole, m.p. 200°–201° C.), 2-isopropoxycarbonylamino (e.g. 4,5-dihydro-2-isopropoxycarbonylamino-4-phenylimidazole) and 2-n-pentoxycarbonylamino derivatives of each of the above compounds are respectively prepared.

EXAMPLE 2

This example illustrates methods according to the invention of preparing the compounds of the invention. In this example, 50 ml. of isopropanol and 1.8 g. of sodium methoxide is added to a solution containing 4.0 g. of the dihydrochloride salt of β-amino-β-(3-methoxyphenyl)-ethylamine dissolved in 10 ml. of water. The mixture is stirred for 15 minutes and then a solution containing 3.4 g. of a mixture of 1-mono and 1,3-bis(methoxycarbonyl)-S-methylisothiourea in 50 ml. of chloroform is added and then stirred for about 2 weeks at room temperature. The mixture is then concentrated by evaporation to dryness and the residue is dissolved in 50 ml. of 1N hydrochloric acid. The acidic solution is washed with ethyl ether, then treated with aqueous sodium bicarbonate, and the precipitate is collected. The collected solid is then stirred with distilled water, refiltered and washed in this manner three more times, then dried overnight at 55° C. affording 3.3 g. of crude product, m.p. 172°–175° C. The crude product is then purified by recrystallization from acetonitrile affording 2.5 g. of 4,5-dihydro-4-(3-methoxyphenyl)-2-methoxycarbonylamino-imidazole, m.p. 176°–177° C.

Similarly, by following the same procedure but using the corresponding substituted phenyl or unsubstituted phenyl-β-amino-ethylamine starting materials in place of β-amino-β-(3-methoxyphenyl)-ethylamine. The following compounds are respectively prepared.
4,5-dihydro-2-methoxycarbonylamino-4-(4-methoxyphenyl)-imidazole;
4,5-dihydro-2-methoxycarbonylamino-4-(2-methoxyphenyl)-imidazole;
4,5-dihydro-4-(4-benzyloxyphenyl)-4-(2-methoxyphenyl)-imidazole, m.p. 221°–223° C., (HCl salt, m.p. 199°–203° C.);
4,5-dihydro-4-(2-ethoxyphenyl)-2-methoxycarbonylaminoimidazole; m.p. 209°–211° C.;
4,5-dihydro-4-(3-ethoxyphenyl)-2-methoxycarbonylaminoimidazole;
4,5-dihydro-4-(4-ethoxyphenyl)-2-methoxycarbonylaminoimidazole;
4,5-dihydro-4-(4-isopropoxyphenyl)-2-methoxycarbonylaminoimidazole;
4-(3-t-butoxyphenyl)-4,5-dihydro-2-methoxycarbonylaminoimidazole;
4,5-dihydro-2-methoxycarbonylamino-4-(3-pentoxyphenyl)-imidazole;
4,5-dihydro-4-(4-hydroxyphenyl)-2-methoxycarbonylaminoimidazole; m.p. 198°–199° C.;

4,5-dihydro-4-(3-hydroxyphenyl)-2-methoxycarbonylaminoimidazole; and
4,5-dihydro-4-(2-hydroxyphenyl)-2-methoxycarbonylaminoimidazole.

Similarly, by following the same procedure but respectively replacing the 1-mono and 1,3-bis(methoxycarbonyl)-S-methylisothiourea mixture with the corresponding 1-mono and 1,3-bis(alkoxycarbonyl)-S-methylisothiourea mixtures, the corresponding 2-ethoxycarbonylamino, 2-isopropoxycarbonylamino and 2-n-pentoxycarbonylamino derivatives of each of the above compounds are respectively prepared.

The nitrate salt ($NHO_3$) of 4,5-dihydro-2-methoxycarbonylamino-4-(3-methoxyphenyl)-imidazole, m.p. 110°–112° C., is prepared by dissolving 4,5-dihydro-2-methoxycarbonylamino-4-(3-methoxyphenyl)-imidazole in a few milliliters of ethanol and an equimolar amount of 70% aqueous nitric acid. The nitrate salt is then caused to crystallize by addition of ethyl ether until the solution turns just slightly turbid. Similarly, by following the same procedure, the nitrate salt of each of the above products is also respectively prepared.

EXAMPLE 3

This example illustrates methods, according to the invention, of preparing the halo substituted phenyl and trifluoromethyl substituted phenyl compounds of the invention. In this example, 5.0 g. of the dihydrochloride salt of β-amino-β-(3-fluorophenyl)-ethylamine is dissolved in 40 ml. of water, then filtered to remove any insoluble impurities and then diluted to a volume of 150 ml. by the addition of isopropanol. 2.4 Grams of sodium methoxide is then added and the resulting mixture stirred for 5 minutes. 4.5 Grams of a mixture of 1-mono and 1,3-bis-(methoxycarbonyl)-S-methylisothiourea in 75 ml. of chloroform is then added and the resulting mixture is stirred for 12 days at room temperature, and then concentrated by evaporation to near dryness. The resulting residue is stirred with water and collected by filtration, dissolved in 70 ml. of 2% aqueous hydrochloric acid, then washed with ethyl ether and benzene and filtered. The filtrate is then treated with saturated aqueous sodium bicarbonate, the resulting precipitate is collected, washed twice with water, and then dried in vacuum affording 3.4 g. of crude product, m.p. 202°–204° C. The crude product is then recrystallized from acetonitrile affording 2.3 g. of 4,5-dihydro-4-(3-fluorophenyl)-2-methoxycarbonylamino-imidazole, m.p. 206°–207° C.

Similarly, by following the same procedure but using the corresponding β-(substituted phenyl)-β-aminoethylamine starting material in place of β-amino-β-(3-fluorophenyl)-ethylamine, the following compounds are respectively prepared.

4,5-dihydro-4-(4-fluorophenyl)-2-methoxycarbonylamino-imidazole;
4,5-dihydro-4-(2-fluorophenyl)-2-methoxycarbonylamino-imidazole; m.p. 203°–204° C., hydrochloride salt m.p. 144°–146° C.;
4-(2-chlorophenyl)-4,5-dihydro-2-methoxycarbonylamino-imidazole; m.p. 203°–204° C., hydrochloride salt, m.p. 160°–162° C.;
4-(4-chlorophenyl)-4,5-dihydro-2-methoxycarbonylamino-imidazole; m.p. 220°–222° C.;
4-(3-chlorophenyl)-4,5-dihydro-2-methoxycarbonylamino-imidazole, m.p. 197°–198° C., HCl salt, m.p. 163°–164° C.;
4-(2-bromophenyl)-4,5-dihydro-2-methoxycarbonylamino-imidazole, m.p. 203°–204° C., HCl salt m.p. 156°–159° C.;
4-(4-bromophenyl)-4,5-dihydro-2-methoxycarbonylamino-imidazole;
4,5-dihydro-4-(3-iodophenyl)-2-methoxycarbonylamino-imidazole;
4,5-dihydro-4-(4-iodophenyl)-2-methoxycarbonylamino-imidazole;
4,5-dihydro-2-methoxycarbonylamino-4-(4-trifluoromethylphenyl)-imidazole, m.p. 229°–230° C.;
4,5-dihydro-2-methoxycarbonylamino-4-(2-trifluoromethylphenyl)-imidazole;
4,5-dihydro-2-methoxycarbonylamino-4-(3-trifluoromethylphenyl)-imidazole; and
4-(3-bromophenyl)-4,5-dihydro-2-methoxycarbonylamino-imidazole, m.p. 207°–208° C., HCl salt, m.p. 173°–174° C.

Similarly, by following the same procedure but respectively replacing the 1-mono and 1,3-bis(methoxycarbonyl)-S-methylisothiourea mixtures with the corresponding 1-mono- and 1,3-bis(alkoxycarbonyl)-S-methylisothiourea mixtures, the corresponding 2-ethoxycarbonylamino, 2-isopropoxycarbonylamino and 2-n-hexoxycarbonylamino derivatives of each of the above compounds are respectively prepared.

The hydrobromide salt of 4,5-dihydro-4-(3-fluorophenyl)-2-methoxycarbonylamino-imidazole, m.p. 142°–143° C., is prepared by treating 4,5-dihydro-4-(3-fluorophenyl)-2-methoxycarbonylamino-imidazole with about an equimolar amount of concentrated hydrobromic acid in acetone. Toluene is added and all solvents removed under pressure affording a gummy residue, which is then refluxed under ethyl ether for 6 hours yielding a solidified hydrobromide salt product.

Similarly, by following the same procedure, the corresponding hydrobromide salts of each of the above compounds are respectively prepared.

EXAMPLE 4

This example illustrates methods according to the invention of preparing the methylenedioxy substituted phenyl compounds of the invention. In this example 9.6 g. of the dihydrochloride salt of β-amino-β-(3,4-methylenedioxyphenyl)-ethylamine is dissolved in 40 ml. of water. This solution is stirred and added successively to it is 150 ml. of isopropanol, 4.1 g. of sodium methoxide and finally 8 g. of a mixture of 1-mono and 1,3-bis(methoxycarbonyl)-S-methylisothiourea in 100 ml of chloroform. The mixture is then stirred for 12 days at room temperature. It is then concentrated under vacuum affording a gummy residue which is then incompletely dissolved in 100 ml. of approximately 1N aqueous hydrochloric acid. The resulting mixture is first filtered and then washed with ethyl ether, heated with charcoal and filtered again. The crude product is then precipitated from the filtrate by addition of aqueous sodium bicarbonate. The precipitate is collected by filtration, stirred with distilled water, collected again and then dried under vacuum affording 2.37 g., m.p. 212°–215° C. of 4,5-dihydro-2-methoxycarbonylamino-4-(3,4-methylenedioxyphenyl)-imidazole. A small sample of this product is recrystallized from isopropanol yielding the purified product, m.p. 214°–216° C.

Similarly, by following the same procedure using the corresponding 1-mono and 1,3-bis(alkoxycarbonyl)-S-methylisothiourea starting material in place of 1,3-bis(- methoxycarbonyl)-S-methylisothiourea, the following compounds are respectively prepared.

4,5-dihydro-2-ethoxycarbonylamino-4-(3,4-methylenedioxyphenyl)-imidazole; and 4,5-dihydro-2-pentoxycarbonylamino-4-(3,4-methylenedioxyphenyl)-imidazole.

The hydrobromide salts of the above compounds are respectively prepared in the same manner as described in Example 3.

EXAMPLE 5

This example illustrates methods according to the invention of preparing the dialkyl substituted phenyl compounds of the invention.

A mixture of 3 g. of the dihydrochloride salt of β-amino-β-(2,5-dimethylphenyl)ethylamine, 35 ml. of saturated sodium bicarbonate solution and 50 ml. of isopropanol is placed in a suitable reaction vessel and stirred for 30 minutes. A solution of 2.5 g. of a mixture of 1-mono- and 1,3-bis(methoxycarbonyl)-S-methylisothiourea in 50 ml of chloroform is then added and the stirring is continued for 4 days. Much of the liquid is evaporated to decrease the volume, then more water is added. The insoluble solid which forms upon addition of the water is collected, dried under vacuum and recrystallized twice, first from a mixture of 100 ml. of isopropanol and 60 ml. of toluene (1.58 g., m.p. 203°–206°) and then from 100 ml. of acetonitrile to give 230 mg. of 4,5-dihydro-4-(2,5-dimethylphenyl)-2-methoxycarbonylaminoimidazole, m.p. 220°–222° C.

Similarly, by following the same procedure but using the corresponding disubstituted phenyl-β-aminoethylamine starting materials in place of β-amino-β-(2,3-dimethylphenyl)-ethylamine, the following compounds are respectively prepared:

4,5-dihydro-4-(2,6-dimethylphenyl)-2-methoxycarbonylaminoimidazole;

4,5-dihydro-4-(2,3-dimethylphenyl)-2-methoxycarbonylaminoimidazole;

4,5-dihydro-4-(2,4-dimethylphenyl)-2-methoxycarbonylaminoimidazole;

4,5-dihydro-4-(3,4-dimethylphenyl)-2-methoxycarbonylaminoimidazole;

4,5-dihydro-4-(3,5-dimethylphenyl)-2-methoxycarbonylaminoimidazole;

4-(3,4-di-t-butylphenyl)-4,5-dihydro-2-methoxycarbonylaminoimidazole;

4-(2,6-di-t-butylphenyl)-4,5-dihydro-2-methoxycarbonylaminoimidazole;

4-(3,5-di-t-butylphenyl)-4,5-dihydro-2-methoxycarbonylaminoimidazole;

4,5-dihydro-4-(2,5-di-n-hexylphenyl)-2-methoxycarbonylaminoimidazole;

4,5-dihydro-4-(2,4-di-n-hexylphenyl)-2-methoxycarbonylaminoimidazole; and 4,5-dihydro-4-(3,4-di-n-hexylphenyl)-2-methoxycarbonylaminoimidazole.

Similarly, by following the same procedure but respectively replacing the 1-mono and 1,3-bis(methoxycarbonyl)-S-methyliothiourea mixture with the corresponding 1-mono- and 1,3-bis(alkoxycarbonyl)-S-methylisothiourea mixtures, the corresponding 2-ethoxycarbonylamino, 2-isopropoxycarbonylamino and 2-n-pentoxycarbonylamino derivatives of each of the above compounds are respectively prepared.

EXAMPLE 6

This example illustrates methods according to the invention of preparing the compounds of the invention.

In this example, 50 ml. of isopropanol and 1.25 g. of sodium methoxide is added to a solution containing 3.0 g. of the dihydrochloride salt of β-amino-β-(3,5-dimethoxyphenyl)-ethylamine dissolved in 10 ml. of water. The mixture is stirred for 15 minutes and then a solution containing 2.6 g. of 1-mono and 1,3-bis(methoxycarbonyl)-S-methylisothiourea mixture in 40 ml. of chloroform is added and then stirred for about 2 weeks at room temperature. The mixture is then concentrated by evaporation to dryness and stirring in 100 ml. of aqueous 0.5 Normal hydrochloric acid for 1 hour. The resulting solution is washed with ethyl ether, then treated with aqueous sodium bicarbonate and filtered. The collected solid is then stirred with distilled water, refiltered, then dried overnight at 55° C. affording 1.68 g. of crude product, m.p. 200°–201° C. The crude product is then purified by recrystallization from 200 ml. of benzene affording 1.14 g. of 4,5-dihydro-4-(3,5-dimethoxyphenyl)-2-methoxycarbonylaminoimidazole, m.p. 202°–203° C.

Similarly, by following the same procedure but using the corresponding substituted phenyl or unsubstituted phenyl -β-amino-ethylamine starting materials in place of β-amino-β-(3,5-dimethoxyphenyl)-ethylamine. The following compounds are respectively prepared.

4,5-dihydro-4-(2,4-dimethoxyphenyl)-2-methoxycarbonylaminoimidazole;

4,5-dihydro-4-(2,3-dimethoxyphenyl)-2-methoxycarbonylaminoimidazole;

4,5-dihydro-4-(2,5-dimethoxyphenyl)-2-methoxycarbonylaminoimidazole;

4,5-dihydro-4-(2,6-dimethoxyphenyl)-2-methoxycarbonylaminoimidazole;

4,5-dihydro-4-(3,4-dimethoxyphenyl)-2-methoxycarbonylaminoimidazole;

4,5-dihydro-4-(2,5-diisopropoxyphenyl)-2-methoxycarbonylaminoimidazole;

4,5-dihydro-4-(2,4-diisopropoxyphenyl)-2-methoxycarbonylaminoimidazole;

4,5-dihydro-4-(3,4-diisopropoxyphenyl)-2-methoxycarbonylaminoimidazole;

4,5-dihydro-4-(2,6-n-hexoxyphenyl)-2-methoxycarbonylaminoimidazole;

4,5-dihydro-4-(3,4-n-hexoxyphenyl)-2-methoxycarbonylaminoimidazole;

4,5-dihydro-4-(3,5-n-hexoxyphenyl)-2-methoxycarbonylaminoimidazole;

4,5-dihydro-4-(3,4-dihydroxyphenyl)-2-methoxycarbonylaminoimidazole; hydrochloride salt m.p. 178°–179° C.;

4,5-dihydro-4-(2,6-dihydroxyphenyl)-2-methoxycarbonylaminoimidazole;

4,5-dihydro-4-(2,5-dihydroxyphenyl)-2-methoxycarbonylaminoimidazole;

4,5-dihydro-4-(2,4-dihydroxyphenyl)-2-methoxycarbonylaminoimidazole; and 4,5-dihydro-4-(3,5-dihydroxyphenyl)-2-methoxycarbonylaminoimidazole.

Similarly, by following the same procedure but respectively replacing the 1-mono and 1,3-bis(methoxycarbonyl)-S-methylisothiourea mixture with the corresponding 1-mono- and 1,3-bis(alkoxycarbonyl)-S-methylisothiourea mixtures, and the corresponding 2-ethoxycarbonylamino, 2-isopropoxycarbonylamino and 2-n-pentoxycarbonylamino derivatives of each of the above compounds are respectively prepared.

The corresponding nitrate salts of the above compounds are respectively prepared in the same manner as described in Example 2.

EXAMPLE 7

This example illustrates methods, according to the invention, of preparing the difluoro substituted phenyl and ditrifluoromethyl substituted phenyl compounds of the invention.

Three grams of the dihydrochloride salt of β-amino-β-(2,5-difluorophenyl)-ethylamine is added to a reaction vessel 25 ml. of a saturated sodium bicarbonate solution. The resulting mixture is stirred and 75 ml. of isopropanol is added thereto followed by a solution of 2.8 g. of a mixture of 1-mono and 1,3-bis(methoxycarbonyl)-S-methylisothiourea in 50 ml. of chloroform. Stirring is continued for 6 days and the mixture is evaporated to dryness. The residue is dissolved in 100 ml. of 0.5 N hydrochloric acid and washed several times with ether and once with toluene. The acidic aqueous solution is then treated with saturated sodium bicarbonate and the resulting precipitate is collected, washed with water and dried in vacuum affording 1.43 g. of a product, m.p. 198°–201° C. Recrystallization from 60 ml of isopropanol-toluene mixture yields 1.13 g. of pure 4,5-dihydro-4-(2,5-difluorophenyl)-2-methoxycarbonylaminoimidazole, m.p. 207°–208° C. A hydrochloride salt is prepared by dissolving the product in ethanolic-hydrogen chloride and crystallizing the salt by slow addition of ether, m.p. 136°–138° C.

Similarly, by following the same procedure but using the corresponding β-(disubstituted phenyl)-β-aminoethylamine starting material in place of β-amino-β-(2,5-difluorophenyl)-ethylamine, the following compounds are respectively prepared:
4,5-dihydro-4-(2,3-difluorophenyl)-2-methoxycarbonylaminoimidazole;
4,5-dihydro-4-(3,4-difluorophenyl)-2-methoxycarbonylaminoimidazole;
4,5-dihydro-4-(2,6-difluorophenyl)-2-methoxycarbonylaminoimidazole;
4,5-dihydro-4-(2,4-difluorophenyl)-2-methoxycarbonylaminoimidazole;
4,5-dihydro-4-(3,5-difluorophenyl)-2-methoxycarbonylaminoimidazole;
4,5-dihydro-2-methoxycarbonylamino-4-(2,3-ditrifluoromethylphenyl)-imidazole;
4,5-dihydro-2-methoxycarbonylamino-4-(2,4-ditrifluoromethylphenyl)-imidazole;
4,5-dihydro-2-methoxycarbonylamino-4-(2,5-ditrifluoromethylphenyl)-imidazole;
4,5-dihydro-2-methoxycarbonylamino-4-(2,6-ditrifluoromethylphenyl)-imidazole;
4,5-dihydro-2-methoxycarbonylamino-4-(3,4-ditrifluoromethylphenyl)-imidazole; and
4,5-dihydro-2-methoxycarbonylamino-4-(3,5-ditrifluoromethylphenyl)-imidazole.

Similarly, by following the same procedure but respectively replacing the 1-mono and 1,3-bis(methoxycarbonyl)-S-methylisothiourea mixture with the corresponding 1-monoand 1,3-bis(alkoxycarbonyl)-S-methylisothiourea mixtures, the corresponding 2-ethoxycarbonylamino, 2-isopropoxycarbonylamino and 2-n-pentoxycarbonylamino derivatives of each of the above compounds are respectively prepared.

EXAMPLE 8

This example illustrates methods, according to the invention, or preparing the dichloro, dibromo, and diiodo substituted phenyl compounds of the invention.

In this example, 3.5 g. of the dihydrochloride salt of β-amino-β-(2,6-dichlorophenyl)ethylamine is added to a suitable reaction vessel containing 30 ml. of saturated sodium bicarbonate. The resulting mixture is stirred, diluted with 50 ml. of isopropanol and a solution of 2.8 g. of a mixture of 1-mono and 1,3-bis(methoxycarbonyl)-S-methylisothiourea in 50 ml. of chloroform is added. Stirring is continued for 6 days and the solvents are removed under vacuum. The residue is stirred with 70 ml. of 2% hydrochloric acid for 30 minutes and the acidic aqueous solution is washed several times with ether, once with toluene and is then treated with excess of saturated sodium bicarbonate. The resulting precipitate is collected by filtration, stirred with water, collected again and dried at 55° under vacuum affording 2.25 g. of 4,5-dihydro-4-(2,6-dichlorophenyl)-2-methoxycarbonylaminoimidazole, m.p. 227°–229° C. A small sample is further purified by recrystallization from toluene to give 4-(2,6-dichlorophenyl)-4,5-dihydro-2-methoxycarbonylaminoimidazole, m.p. 230°–231°.

The hydrosulfate salt of this compound is prepared by dissolving 1.75 g. of the free base in a freshly prepared solution of 750 mg. of sulfuric acid in ethanol. The resulting solution is added dropwise to 300 ml. of well-stirred ether, affording the salt as a white precipitate which is collected, dried in vacuum, to give 2.25 g. of the hydrosulfate salt of 4-(2,6-dichlorophenyl)-4,5-dihydro-2-methoxycarbonylaminoimidazole, m.p. 161°–164° C.

Similarly, by following the same procedure but using the corresponding β-(4-substituted phenyl)-β-aminoethylamino starting material in place of β-amino-β-(2,6-dichlorophenyl)-ethylamine, the following compounds are respectively prepared.
4,5-dihydro-4-(2,3-dichlorophenyl)-2-methoxycarbonylaminoimidazole;
4,5-dihydro-4-(2,5-dichlorophenyl)-2-methoxycarbonylaminoimidazole;
4,5-dihydro-4-(3,4-dichlorophenyl)-2-methoxycarbonylaminoimidazole;
4,5-dihydro-4-(2,4-dichlorophenyl)-2-methoxycarbonylaminoimidazole;
4,5-dihydro-4-(3,5-dichlorophenyl)-2-methoxycarbonylaminoimidazole;
4-(3,4-dibromophenyl)-4,5-dihydro-2-methoxycarbonylaminoimidazole;
4-(2,6-dibromophenyl)-4,5-dihydro-2-methoxycarbonylaminoimidazole;
4-(3,5-dibromophenyl)-4,5-dihydro-2-methoxycarbonylaminoimidazole;
4,5-dihydro-4-(2,5-diiodophenyl)-2-methoxycarbonylaminoimidazole;
4,5-dihydro-4-(2,3-diiodophenyl)-2-methoxycarbonylaminoimidazole; and
4,5-dihydro-4-(2,6-diiodophenyl)-2-methoxycarbonylaminoimidazole.

Similarly, by following the same procedure but respectively replacing the 1-mono and 1,3-bis(methoxycarbonyl)-S-methylisothiourea mixture with the corresponding 1-mono- and 1,3-bis(alkoxycarbonyl)-S-methylisothiourea mixtures, the corresponding 2-ethoxycarbonylamino, 2-isopropoxycarbonylamino and 2-n- pentoxycarbonylamino derivatives of each of the above compounds are respectively prepared.

EXAMPLE 9

This example illustrates methods, according to the invention, of preparing the 2-alkoxycarbonylamino compounds of the invention where a mixture of the mono and the 1,3-bis(alkoxycarbonylamino)-S-methylisothiourea is prepared and used in situ. In this example a mixture of 2.5 g. of S-methyl-2-thiopseudourea sulfate, 4 g. of iso-butyl chloroformate and 8 ml. of water is stirred in an ice bath. To this mixture is added 5.5 ml. of 20%, by wt., of aqueous sodium hydroxide, in three portions and stirring is continued for 2 hours after which time the mixture is extracted with 30 ml. of chloroform. This chloroform extract is added to a stirred mixture of 3 g. of β-amino-β-phenylethylamine dihydrochloride and 12 ml. of 10%, by wt., of aqueous sodium hydroxide in 30 ml. of isopropanol. After ten days, the mixture is evaporated in vacuo to dryness and the residue is stirred with 100 ml. of 0.5N hydrochloric acid for 20 minutes. The resulting solution is washed with ethyl ether four times and twice with toluene. Saturated solution of aqueous sodium bicarbonate is added and the resulting precipitate is collected, stirred with distilled water, recollected and dried in vacuo at 55° C., affording 1.84 g. of crude 2-iso-butoxycarbonylamino-4,5-dihydro-4-phenylimidazole, m.p. 184°–187° C. Recrystallization from 20 ml. of benzene gives 1.5 g. of pure product, m.p. 192°–193° C.

Similarly, by following the same procedure but using the corresponding β-amino-β-substituted phenyl-ethylamines as starting materials, the corresponding 2-iso-butoxycarbonylamino derivatives of each of the free base products, prepared in Examples 1–8, are respectively prepared.

Similarly, by following the same procedure but using the corresponding alkyl chloroformate and β-amino-β-phenyl (or substituted phenyl)-ethylamine dihydrochloride starting materials, the following compounds are respectively prepared:
2-ethoxycarbonylamino-4,5-dihydro-4-phenylimidazole, m.p. 210°–211° C.;
2-ethoxycarbonylamino-4,5-dihydro-4-(4-isopropylphenyl)-imidazole, m.p. 200°–201° C.;
4,5-dihydro-2-hexoxycarbonylamino-4-(4-chlorophenyl)-imidazole, m.p. 201°–203° C.;
4-(3-bromphenyl)-2-ethoxycarbonylamino-4,5-dihydroimidazole, m.p. 191°–193° C.; and
4-(3-chlorophenyl)-4,5-dihydro-2-isopropoxycarbonylamino-imidazole, m.p. 194°–196° C.

EXAMPLE 10

This example illustrates methods, according to the invention, of preparing the 2-n-hexyloxycarbonylamino compounds of the invention. In this example, 5.0 g. of the dihydrochloride salt of β-amino-β-phenylethylamine is dissolved in 40 ml. of water, then filtered to remove any insoluble impurities and then diluted to a volume of 150 ml. by the addition of isopropanol. 2.4 Grams of sodium methoxide are then added and the resulting mixture stirred for 5 minutes. 4.5 Grams of a mixture of mono and 1,3-bis(n-hexoxycarbonyl)-S-methylisothiourea in 75 ml. of chloroform are then added and the resulting mixture is stirred for 12 days at room temperature, and then concentrated by evaporation to near dryness. The resulting residue is stirred with water and collected by filtration, dissolved in 70 ml. of 2% aqueous hydrochloric acid, then washed with ethyl ether and benzene and filtered. The collected solid is then treated with saturated aqueous sodium bicarbonate, filtered, washed twice with water, and then dried in vacuum affording a crude 2-n-hexyloxycarbonylamino-4-phenylimidazole product, which is then further purified by recrystallization from methanol.

Similarly, by following the same procedure but using the corresponding β-amino-β-(substituted phenyl)-ethylamine as starting materials, the corresponding 2-n-hexyloxycarbonylamino derivatives of each of the free base products, prepared in Examples 1–8, are respectively prepared.

EXAMPLE 11

This example illustrates another process embodiment of the invention for preparing compounds of the invention from the corresponding 2-amino-4,5-dihydro-4-(phenyl or substituted phenyl)-imidazole. In this example, 33 g. of 2-amino-4-phenyl-2-imidazoline hydrobromide is stirred in a solution of one molar equivalent (7.4 g.) of sodium methoxide in excess isopropyl alcohol. After about ca. 20 minutes, the mixture is filtered and the filtrate is concentrated under reduced pressure. The residue is refluxed for 2½ hours with 300 ml. of dimethyl carbonate during which time a total of 60 ml. of the refluxing solvent is removed by means of a Dean-Stark trap. The mixture is cooled to room temperature and the solid collected and recrystallized from 800 ml. of methanol, affording 7.34 g. of 4,5-dihydro-2-methoxycarbonylamino-4-phenylimidazole, m.p. 209°–210° C.

Similarly, by following the same procedure but using the corresponding 2-amino-4-substituted phenyl-2-imidazoline hydrobromide and the corresponding dialkylcarbonates as starting materials, the free base products of Examples 1–10, are respectively prepared.

The hydrochloride salt of 4,5-dihydro-2-methoxycarbonylamino-4-phenylimidazole, m.p. 168° C., is prepared by dissolving the corresponding free base (i.e. 4,5-dihydro-2-methoxycarbonylamino-4-phenylimidazole) in 0.5N hydrochloric acid and then removing most of the water under reduced pressure. Residual amounts of water are removed by addition of isopropanol and toluene and subsequent removal of the solvent under reduced pressure. The resulting solid hydrochloride salt can be recrystallized from isopropanol. Similarly, by following the same procedure, the hydrochloride salt of each of the above products is also respectively prepared.

EXAMPLE 12

This example illustrates the preparation of the pure (+) optical isomers of the invention. In this example, starting with 2.0 g. (+) β-amino-β-phenylethylamine and following the procedure of Example 1, there is obtained 1.98 g. of (+) 4,5-dihydro-2-methoxycarbonylamino-4-phenylimidazole, m.p. 219°–220° C.; $[\alpha]_D^{25}$ + 50.7° (C: 0.5% in dimethyl sulfoxide). Similarly, the corresponding (+) isomers of the products prepared in Examples 1–11 are respectively prepared by repeating the procedures of Examples 1–11 but using the respective pure (+) optical isomers of β-amino-β-substituted phenyl-ethylamine as starting materials in Examples 1–10 and the respective pure (+) optical isomers of 2-amino-4,5-dihydro-4-(phenyl or substituted phenyl)imidazole as starting materials in Example 11, in place of the racemic starting materials.

EXAMPLE 13

This example illustrates methods according to the invention of preparing mono- and dihydroxy substituted phenyl compounds of the invention. In this example, 2.8 g. of β-amino-β-(3,4-dibenzyloxyphenyl)ethylamine is dissolved in 50 ml. of ethanol and 2 ml. of water. This solution is combined with a solution of 1.7 g. of a mixture of 1-mono and 1,3-bis (methoxycarbonyl)-S-methylisothiourea in 25 ml. of chloroform and allowed to stand for 8 days and then concentrated to dryness. The residue is treated with 100 ml. of 0.5N hydrochloric acid and the resulting slurry is stirred vigorously in the presence of ethyl ether. Stirring is discontinued and the ether layer is removed by decantation. This process is repeated four times and the remaining aqueous slurry is then treated in the excess of saturated aqueous sodium bicarbonate solution. The product, 4,5-dihydro-4-(3,4-dibenzyloxyphenyl)-2-methoxycarbonylaminoimidazoline, is extracted into chloroform, the chloroform is removed and the remaining product is purified by recrystallization from 300 ml. of benzene, 1.25 g.; m.p. 189°–191°. By treating the resulting free base with a solution of 10 ml. of ethanol that contains 400 mg. of hydrogen chloride and then with 200 ml of ether, 1.27 g. of the hydrochloride salt, m.p. 136°–140° C. is obtained. A sample of 1.2 g of the hydrochloride salt of 4,5-dihydro-4-(3,4-dibenzyloxyphenyl)-2-methoxycarbonylaminoimidazole is treated according to a standard hydrogenolysis procedure using 500 mlg. of palladium-on-charcoal catalyst in 50 ml. ethanol and hydrogen gas at atmospheric pressure, to afford 600 mg., of the hydrochloride salt of 4,5-dihydro-4-(3,4-dihydroxyphenyl)-methoxycarbonylaminoimidazole m.p. 178°–179°.

Similarly, by following the same procedure but using the appropriate β-amino-β-([di]benzyloxyphenyl)ethylamine, other mono- or dihydroxyphenyl compounds may be prepared such as 4,5-dihydro-4-(2-hydroxyphenyl)-2-methoxycarbonylaminoimidazole;
4,5-dihydro-4-(3-hydroxyphenyl)-2-methoxycarbonylaminoimidazole;
4,5-dihydro-4-(4-hydroxyphenyl)-2-methoxycarbonylaminoimidazole as hydrochloride salt, m.p. 180°–183° C.;
4,5-dihydro-4-(2,6-dihydroxyphenyl)-2-methoxycarbonylaminoimidazole;
4,5-dihydro-4-(2,5-dihydroxyphenyl)-2-methoxycarbonylaminoimidazole;
4,5-dihydro-4-(2,4-dihydroxyphenyl)-2-methoxycarbonylaminoimidazole;
4,5-dihydro-4-(2,3-dihydroxyphenyl)-2-methoxycarbonylaminoimidazole; and
4,5-dihydro-4-(3,5-dihydroxyphenyl)-2-methoxycarbonylaminoimidazole.

EXAMPLE 14

This example illustrates the preparation of the pure (−) optical isomers of the invention. In this example, starting with 2.1 g. of (−) β-amino-β-phenylethylamine and following the procedure of Example 1, there is obtained 2.09 g. of (−) 4,5-dihydro-2-methoxycarbonylamino-4-phenylimidazole, m.p. 221°–223° C.; $[\alpha]_D^{25}$ − 51.6° (C: 0.5% in dimethyl sulfoxide).

Similarly, the corresponding (−) isomers of the products prepared in Examples 1–11 are respectively prepared by repeating the procedures of Examples 1–11 but using the respective pure (−) optical isomers of β-amino-β-phenyl (or substituted phenyl)-ethylamine as starting materials in Examples 1–10 and the respective pure (−) optical isomers of 2-amino-4,5-dihydro-4-(phenyl or substituted phenyl)imidazole as starting materials in Example 11, in place of the racemic starting materials.

EXAMPLE 15

The example illustrates methods for preparing the pharmaceutically acceptable salts of the invention.

In this example, 500 mg. of 4,5-dihydro-2-methoxycarbonylamino-4-phenylimidazole and 265 mg. of maleic acid are refluxed together in 50 ml. of methylenechloride until only traces of insoluble materials are left. The solution is filtered and the filtrate is treated with ethyl ether. The resulting precipitate maleate salt is collected by filtration and dried under vacuum, affording 630 mg. of the maleate salt of 4,5-dihydro-2-methoxycarbonylamino-4-phenylimidazole, m.p. 174°–175° C.

Similarly, by following the same procedure, but respectively using the free base products of Examples 1–13, the corresponding maleate salts of these products are respectively prepared.

EXAMPLE 16

This example illustrates another process embodiment of the invention wherein an alkyl chloroformate is used as one of the reagents. In this example, 0.8 g. of methyl chloroformate is added over a five minute period to a stirring mixture of 2 g. 2-amino-4-phenyl-2-imidazoline hydrobromide, 1.4 g. sodium bicarbonate, and 20 ml. acetone held at 0° C. After addition is complete, the mixture is allowed to warm to room temperature and then stirred for 16 hours at room temperature. The mixture is distilled to a low volume and 50 ml. of water is then added. The mixture is filtered and the precipitate collected and washed with water and then dried affording 4,5-dihydro-2-methoxycarbonylamino-4-phenylimidazole which is then further purified by recrystallizaton from chloroform.

Similarly, by following the same procedure but using the corresponding 2-amino-4-substituted phenyl-2-imidazoline hydrobromide and the corresponding alkyl chloroformates as starting materials, the free base products of Examples 1–10, are respectively prepared.

EXAMPLE 17

This example illustrates the process of the invention wherein 1-(mono)-alkoxycarbonyl-S-methylisothiourea is used in placed of a mixture of the mono- and bis-alkoxycarbonyl reagents.

Aqueous sodium bicarbonate is added to a suitable reaction vessel containing a solution of 0.6 g. of the dihydrochloride of β-amino-β-(3-chlorophenyl)ethylamine in a few ml. of water followed by 100 ml of isopropanol and a solution of 0.7 g. of 1-(mono)-isopropoxycarbonyl-S-methylisothiourea in 25 ml. of chloroform. The resulting mixture is stirred for 3 days at ambient temperature, concentrated to dryness on a rotary evaporator and the residue is dissolved in dilute hydrochloric acid. The aqueous solution is washed twice with ether and once with toluene, and then is treated with excess of saturated sodium bicarbonate. The resulting white precipitate is collected by filtration, suspended in water, collected by filtration again, and dried in vacuum to give 130 mg. of 4,5-dihydro-4-(3-chlorophenyl)-2-isopropoxycarbonylaminoimidazole, m.p. 194°–196°.

Similarly, the free base products of Examples 1-9 are respectively prepared by following the procedures of these examples but replacing the 1-mono- and 1,3-bis-alkoxycarbonyl-S-methylisothiourea mixtures, used in Examples 1-9, with the corresponding 1-alkoxycarbonyl-S-methylisothiourea.

EXAMPLE 18

This example illustrates the process of the invention for preparing 4,5-dihydro-2-alkoxycarbonylamino-4-phenylimidazoles.

A solution of 0.42 g. β-amino-β-phenylethylaminodihydrochloride in 3 ml. water is treated with 0.34 g. sodium bicarbonate. The mixture is stirred briefly and a solution of 0.42 g. 1,3-bismethoxycarbonyl-2-methylthiourea in 6 ml. methanol is added. The mixture is heated to reflux for 2 hours whereupon 3 ml. methanol are distilled out. The mixture is cooled and the precipitate is filtered off. The white crystalline precipitate is washed with methanol and water and is dried, yielding 0.4 g. (90%) of 4,5-dihydro-2-methoxycarbonylamino-4-phenyl-imidazole. Similarly, by following the above procedure but substituting other 1,3-bisalkoxycarbonyl-2-methylureas for 1,3-bismethoxycarbonyl-2-methylurea, other compounds of this invention are prepared.

Obviously many modifications and variations of the invention, described hereinabove and below in the claims, can be made without departing from the scope and essence thereof.

What is claimed is:

1. A compound having the formula

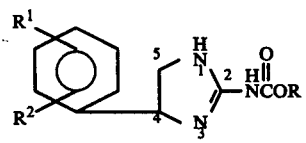

wherein R is lower alkyl; $R^1$ is hydrogen, lower alkyl, hydroxy, lower alkoxy, fluoro, chloro, bromo, iodo or trifluoromethyl and $R^2$ is hydrogen or is a substituent which is identical to the $R^1$ substituent and wherein $R^1$ and $R^2$ can each be at any different position on the phenyl ring or $R^1$ and $R^2$ together form methylenedioxy and are at adjacent carbon atoms on the phenyl ring; and pharmaceutically acceptable salts thereof.

2. A compound selected from those represented by the formula

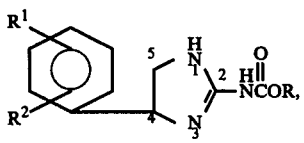

wherein
 (a) R is methyl, $R^1$ is hydrogen and $R^2$ is hydrogen, halo, methyl, ethyl, hydroxy, methoxy, alkoxy of 2 through 6 carbons, alkyl of one through six carbons or trifluoromethyl;
 (b) R is methyl and $R^1$ and $R^2$ together are dihalo, dimethoxy, dialkoxy of 2 through 6 carbon atoms, dihydroxy, dimethyl and diethyl;
 (c) R is methyl and $R^1$ and $R^2$ together are 3,4-methylenedioxy;
 (d) R is ethyl, $R^1$ is hydrogen, and $R^2$ is methoxy, ethoxy, hydroxy, hydrogen, halo, methyl or ethyl;
 (e) R is ethyl and $R^1$ and $R^2$ together are dichloro, difluoro, dihydroxy, dimethyl or dimethoxy; and
 (f) R is alkyl of 3 or 4 carbon atoms, $R^1$ is hydrogen and $R^2$ is hydrogen, fluoro or chloro; and the pharmaceutically acceptable salts thereof.

3. The compound of claim 2 chosen from those represented by formula (I) wherein
 (a) R is methyl, $R^1$ is hydrogen and $R^2$ is hydrogen, halo, hydroxy, 2-methoxy or methyl;
 (b) R is methyl and $R^1$ and $R^2$ together are dichloro, difluoro, dimethoxy or dihydroxy;
 (c) R is methyl and $R^1$ and $R^2$ together are 2,6-diethoxy, 2,6-dibromo, 2,3-dibromo, 2,4-dibromo, 2,5-dibromo, 2,6-diiodo, 2,5-diiodo or 2,3-diiodo;
 (d) R is ethyl and $R^1$ and $R^2$ are both hydrogen or are together 2,5-, 2,6-, 2,4- or 2,3-difluoro, 2,6-, 2,5-, 2,4- or 2,3-dihydroxy, or dimethoxy;
 (e) R is ethyl, $R^1$ is hydrogen and $R^2$ is halo, methyl, ethyl, methoxy, ethoxy or hydroxy;
 (f) R is alkyl of 3 or 4 carbon atoms, $R^1$ is hydrogen and $R^2$ is hydrogen, fluoro or chloro; and the pharmaceutically acceptable salts thereof.

4. The compound of claim 3 wherein R is methyl, $R^1$ is hydrogen and $R^2$ is fluoro, chloro, methyl, hydroxy or hydrogen.

5. The compound of claim 4 wherein $R^2$ is chloro or fluoro.

6. The compound of claim 5 wherein $R^2$ is fluoro.

7. The compound of claim 6 wherein said compound is selected from the group of 4,5-dihydro-4-(2-fluorophenyl)-2-methoxycarbonylaminoimidazole and pharmaceutically acceptable salts thereof.

8. The compound of claim 6 wherein said compound is selected from the group of 4,5-dihydro-4-(3-fluorophenyl)-2-methoxycarbonylaminoimidazole and pharmaceutically acceptable salts thereof.

9. The compound of claim 6 wherein said compound is selected from the group of 4,5-dihydro-4-(4-fluorophenyl)-2-methoxycarbonylaminoimidazole and pharmaceutically acceptable salts thereof.

10. The compound of claim 5 wherein said $R^2$ is chloro.

11. The compound of claim 10 wherein said compound is selected from the group of 4,5-dihydro-4-(2-chlorophenyl)-2-methoxycarbonylaminoimidazole and pharmaceutically acceptable salts thereof.

12. The compound of claim 10 wherein said compound is selected from the group of 4,5-dihydro-4-(3-chlorophenyl)-2-methoxycarbonylaminoimidazole and pharmaceutically acceptable salts thereof.

13. The compound of claim 10 wherein said compound is selected from the group 4,5-dihydro-4-(4-chlorophenyl)-2-methoxycarbonylaminoimidazole and pharmaceutically acceptable salts thereof.

14. The compound of claim 4 wherein $R^2$ is methyl.

15. The compound of claim 14 wherein said compound is selected from the group of 4,5-dihydro-4-(3-methylphenyl)-2-methoxycarbonylaminoimidazole and pharmaceutically acceptable salts thereof.

16. The compound of claim 14 wherein said compound is selected from the group of 4,5-dihydro-4-(2-methylphenyl)-2-methoxycarbonylaminoimidazole and pharmaceutically acceptable salts thereof.

17. The compound of claim 14 wherein said compound is selected from the group of 4,5-dihydro-4-(4- methylphenyl)-2-methoxycarbonylaminoimidazole and the pharmaceutically acceptable salts thereof.

18. The compound of claim 4 wherein said compound is selected from the group of 4,5-dihydro-4-(4-hydroxyphenyl)-2-methoxycarbonylaminoimidazole and pharmaceutically acceptable salts thereof.

19. The compound of claim 4 wherein said compound is selected from the group of 4,5-dihydro-4-phenyl-2-methoxycarbonylaminoimidazole and pharmaceutically acceptable salts thereof.

20. The compound of claim 3 wherein R is methyl and $R^1$ and $R^2$ together are dichloro, difluoro, dimethoxy or dihydroxy.

21. The compound of claim 20 wherein $R^1$ and $R^2$ are both fluoro.

22. The compound of claim 21 wherein said compound is selected from the group of 4,5-dihydro-4-(2,4-difluorophenyl)-2-methoxycarbonylaminoimidazole and pharmaceutically acceptable salts thereof.

23. The compound of claim 21 wherein said compound is selected from the group of 4,5-dihydro-4-(3,4-difluorophenyl)-2-methoxycarbonylaminoimidazole and pharmaceutically acceptable salts thereof.

24. The compound of claim 21 wherein said compound is selected from the group of 4,5-dihydro-4-(2,6-difluorophenyl)-2-methoxycarbonylaminoimidazole and pharmaceutically acceptable salts thereof.

25. The compound of claim 21 wherein said compound is selected from the group of 4,5-dihydro-4-(2,5-difluorophenyl)-2-methoxycarbonylaminoimidazole and pharmaceutically acceptable salts thereof.

26. The compound of claim 21 wherein said compound is selected from the group of 4,5-dihydro-4-(2,3-difluorophenyl)-2-methoxycarbonylaminoimidazole and pharmaceutically acceptable salts thereof.

27. The compound of claim 21 wherein said compound is selected from the group of 4,5-dihydro-4-(3,5-difluorophenyl)-2-methoxycarbonylaminoimidazole and pharmaceutically acceptable salts thereof.

28. The compound of claim 20 wherein $R^1$ and $R^2$ are each chloro.

29. The compound of claim 28 wherein said compound is selected from the group of 4,5-dihydro-4-(2,6-dichlorophenyl)-2-methoxycarbonylaminoimidazole and pharmaceutically acceptable salts thereof.

30. The compound of claim 2 selected from those represented by formula (I), wherein
  (a) R is methyl or ethyl and $R^1$ and $R^2$ are independently chosen from hydrogen and fluoro;
  (b) R is methyl, $R^1$ is hydrogen and $R^2$ is ethyl, chloro, 2-bromo, 3-bromo, 2-methyl and 3-methyl; and
  (c) R is methyl, and $R^1$ and $R^2$ together are 2,3-, 2,4-, 2,5-, or 3,5-dimethyl.

31. The compound of claim 30 wherein said compound is selected from the group of 4,5-dihydro-4-phenyl-2-ethoxycarbonylaminoimidazole and pharmaceutically acceptable salts thereof.

32. The compound of claim 30 wherein R is methyl, $R^1$ is hydrogen and $R^2$ is ethyl.

33. The compound of claim 32 wherein said compound is selected from the group 4,5-dihydro-4-(4-ethylphenyl)-2-methoxycarbonylaminoimidazole and the pharmaceutically acceptable salts thereof.

34. The compound of claim 30 wherein R is methyl, $R^1$ and $R^2$ together are 2,3-, 2,4-, 2,5-, or 3,5-dimethyl and pharmaceutically acceptable salts thereof.

35. The compound of claim 34 wherein said compound is selected from the group of 4,5-dihydro-4-(2,5-dimethylphenyl)-2-methoxycarbonylaminoimidazole and pharmaceutically acceptable salts thereof.

36. The compound of claim 34 wherein said compound is selected from the group of 4,5-dihydro-4-(3,5-dimethylphenyl)-2-methoxycarbonylaminoimidazole and pharmaceutically acceptable salts thereof.

37. The compound of claim 2 selected from those represented by formula (I), wherein
  (a) R is methyl, $R^1$ is hydrogen and $R^2$ is fluoro, chloro, alkyl of one through six carbon atoms, alkoxy of two through six carbon atoms, trifluoromethyl, 2-iodo 3-methoxy or 4-methoxy;
  (b) R is methyl and $R^1$ and $R^2$ together are dialkoxy of 2 through 6 carbon atoms, dichloro, 2,6-dibromo, or 3,5-dimethyl;
  (c) R is ethyl, $R^1$ and $R^2$ together are dihydroxy, difluoro, dichloro, dimethyl or dimethoxy;
  (d) R is methyl and $R^1$ and $R^2$ together are 3,4-methylenedioxy;
  (e) R is alkyl of 2 or 3 carbon atoms and $R^1$ and $R^2$ are both hydrogen and the pharmaceutically acceptable salts thereof.

38. The compound of claim 37 wherein said compound is selected from the group of 4,5-dihydro-2-methoxycarbonylamino-2-(3,4-methylenedioxyphenyl)-imidazole or a pharmaceutically acceptable salt thereof.

39. The compound of claim 37 wherein said compound is selected from the group of 4,5-dihydro-4-(2-iodophenyl)-2-methoxycarbonylaminoimidazole and pharmaceutically acceptable salts thereof.

40. The compound of claim 37 wherein said compound is selected from the group of 4,5-dihydro-4-(2,6-dibromophenyl)-2-methoxycarbonylaminoimidazole and pharmaceutically acceptable salts thereof.

41. The compound of claim 37 wherein R is methyl, $R^1$ is hydrogen and $R^2$ is trifluoromethyl.

42. The compound of claim 37 wherein $R^1$ and $R^2$ are each identical alkoxy groups of 2 through 6 carbons and R is methyl.

43. The compound of claim 37 wherein said compound is selected from the group of 4,5-dihydro-4-(4-ethoxyphenyl)-2-methoxycarbonylaminoimidazole, 4,5-dihydro-4-(2-ethoxyphenyl)-2-methoxycarbonylaminoimidazole; and pharmaceutically acceptable salts thereof.

44. The compound of claim 37 wherein $R^2$ is alkyl of 1 through 6 carbons, $R^1$ is hydrogen and R is methyl.

45. The compound of claim 44 wherein said compound is selected from the group of 4,5-dihydro-4-(4-n-hexylphenyl)-2-methoxycarbonylaminoimidazole and the pharmaceutically acceptable salts thereof.

46. The compound of claim 2 chosen from those represented by formula (I) wherein
  (a) R is methyl, $R^1$ is hydrogen and $R^2$ is 2- or 3-methyl, 2- or 3-ethyl, 2-iodo, 3-fluoro, 2-ethoxy or 3-methoxy;
  (b) R is methyl, $R^1$ is iodo, ethyl, isopropoxy, n-propoxy or ethoxy at the 2-position of the phenyl ring and $R^2$ is the same as $R^1$ at any other position on the phenyl ring; and
  (c) R is methyl, $R^1$ and $R^2$ together are 2,6-, 2,5-, or 2,3-dibromo; 2,3- or 2,5-dichloro; 2,6-, 2,5- or 2,3-dimethyl; or 2,3- or 2,5-dimethoxy;
  (d) R is ethyl, $R^1$ is hydrogen and $R^2$ is 2-iodo or 2-ethyl;

(e) R is ethyl and $R^1$ and $R^2$ together are 2,6-, 2,5- or 2,3-diethyl, 2,5- or 2,3-diethoxy, difluoro, dichloro, dimethyl, dimethoxy or dihydroxy; and the pharmaceutical salts thereof.

47. The compound of claim 46 wherein R is methyl, $R^1$ is 2-ethoxy and $R^2$ is ethoxy and pharmaceutically acceptable salts thereof.

48. The compound of claim 47 wherein said compound is selected from the group consisting of 4,5-dihydro-4-(2,4-diethoxyphenyl)-2-methoxycarbonylaminoimidazole and pharmaceutically acceptable salts thereof.

49. The compound of claim 46 wherein R is methyl.

50. The compound of claim 46 wherein said compound is selected from the group of 4,5-dihydro-4-(3-methoxyphenyl)-2-methoxycarbonylaminoimidazole, and pharmaceutically acceptable salts thereof.

51. The compound of claim 46 wherein $R^1$ and $R^2$ are each iodo and said compound is selected from the group consisting of 4,5-dihydro-4-(2,6-diiodophenyl)-2-methoxycarbonylaminoimidazole and pharmaceutically acceptable salts thereof.

52. A pharmaceutical composition useful for palliating, treating or preventing depressive illness in a mammal, which composition comprises an effective amount of the compound of claim 3 and a pharmaceutically acceptable carrier.

53. A pharmaceutical composition useful for palliating, treating or preventing depressive illness in a mammal, which composition comprises an effective amount of the compound of claim 5 and a pharmaceutically acceptable carrier.

54. A pharmaceutical composition useful for palliating, treating or preventing depressive illness in a mammal, which composition comprises an effective amount of the compound of claim 20 and a pharmaceutically acceptable carrier.

55. A pharmaceutical composition useful for palliating, treating or preventing depressive illness in a mammal, which composition comprises an effective amount of the compound of claim 21 and a pharmaceutically acceptable carrier.

56. A pharmaceutical composition useful for palliating, treating or preventing depressive illness in a mammal, which composition comprises an effective amount of the compound of claim 28 and a pharmaceutically acceptable carrier.

57. The composition of claim 56 wherein said compound is selected from the group consisting of 4,5-dihydro-4-(2,6-dichlorophenyl)-2-methoxycarbonylaminoimidazole and the pharmaceutically acceptable salts thereof.

58. A method of palliating, treating or preventing depressive illness in a mammal, which comprises administering to said mammals an effective amount of about 0.01 to 200 mg/kg of a compound according to claim 3.

59. A method of palliating, treating or preventing depressive illness in a mammal, which comprises administering to said mammals an effective amount of about 0.01 to 200 mg/kg of a compound according to claim 5.

60. A method of palliating, treating or preventing depressive illness in a mammal, which comprises administering to said mammals an effective amount of about 0.01 to 200 mg/kg of a compound according to claim 20.

61. A method of palliating, treating or preventing depressive illness in mammals, which comprises administering to said mammals an effective amount of about 0.01 to 200 l mg/kg of a compound according to claim 21.

62. A method of palliating, treating or preventing depressive illness in mammals, which comprises administering to said mammals an effective amount of about 0.01 to 200 mg/kg of a compound according to claim 28.

63. The method of claim 62 wherein said compound is selected from the group consisting of 4,5-dihydro-4-(2,6-dichlorophenyl)-2-methoxycarbonylaminoimidazole and the pharmaceutically acceptable salts thereof.

64. A pharmaceutical composition useful for preventing or reducing the frequency of or severity of convulsions, in a mammal which is subject to convulsions, which are etiopathic to the central nervous system, which composition comprises an effective amount of the compound of claim 30 and a pharmaceutically acceptable carrier.

65. A pharmaceutical composition useful for preventing or reducing the frequency of or severity of convulsions, in a mammal which is subject to convulsions which are etiopathic to the central nervous system, which composition comprises an effective amount of the compound of claim 5 and a pharmaceutically acceptable carrier.

66. A method of preventing or reducing the frequency of or severity of convulsions, in a mammal which is subject to convulsions which are etiopathic to the central nervous system, which comprises administering to said mammal an effective amount, of about from 0.01 to 200 mg/kg of a compound according to claim 30.

67. A method of preventing or reducing the frequency of or severity of convulsions, in a mammal which is subject to convulsions which are etiopathic to the central nervous system, which comprises administering to said mammal an effective amount, of about from 0.01 to 200 mg/kg of a compound according to claim 5.

68. A pharmaceutical composition useful for reducing or preventing the frequency or intensity of centrally induced skeletal muscle spasms, in a mammal which is subject to such spasms which are etiopathic to the central nervous system, which composition comprises an effective amount of the compound of claim 37 and a pharmaceutically acceptable carrier.

69. A pharmaceutical composition useful for reducing or preventing the frequency or intensity of centrally induced skeletal muscle spasms, in a mammal which is subject to such spasms which are etiopathic to the central nervous system, which composition comprises an effective amount of the compound of claim 5 and a pharmaceutically acceptable carrier.

70. A method of reducing or preventing the frequency or intensity of centrally induced skeletal muscle spasms, in a mammal which is subject to such spasms which are etiopathic to the central nervous system, which method comprises administering to said mammal an effective amount, of about 0.01 to 200 mg/kg of a compound according to claim 37.

71. A method of reducing or preventing the frequency or intensity of centrally induced skeletal muscle spasms, in a mammal which is subject to such spasms which are etiopathic to the central nervous system, which method comprises administering to said mammal an effective amount, of about 0.01 to 200 mg/kg of a compound according to claim 5.

72. A pharmaceutical composition useful for producing a neuroleptic effect in a mammal which comprises an effective amount of the compound of claim 46 and a pharmaceutically acceptable carrier.

73. A method of producing a neuroleptic effect in a mammal, which comprises administering an effective amount of about 0.01 to 200 mg/kg, of a compound according to claim 46 to said mammal.

74. A pharmaceutical composition useful for treating, palliating or preventing abnormal conditions related to the central nervous system, in a mammal, such as depressive illness, epileptic or convulsant siezures states, anxiety, and disorders involving muscle spasms or spasticity, which composition comprises an effective amount of the compound of claim 1 and a pharmaceutically acceptable carrier.

75. A method for treating, palliating or preventing abnormal conditions related to the central nervous system, in a mammal, such as depressive illness, epileptic or convulsant siezure states, anxiety, and disorders involving muscle spasms or spasticity which method comprises administering an effective amount of the compound of claim 1 to said mammal.

76. A pharmaceutical composition useful for treating, palliating, or preventing abnormal conditions related to the central nervous system, in a mammal, such as depressive illness, epileptic or convulsant seizure states, anxiety, and disorders involving muscle spasms or spasticity which composition comprises an effective amount of the compound of claim 2 and a pharmaceutically acceptable carrier.

77. A method for treating palliating or preventing abnormal conditions related to the central nervous system, in a mammal, such as depressive illness, epileptic or convulsant siezure states, anxiety, and disorders involving muscle spasms or spasticity which method comprises administering an effective amount of the compound of claim 2 to said mammal.

* * * * *